US012613233B2

(12) United States Patent
Schimmel et al.

(10) Patent No.: US 12,613,233 B2
(45) Date of Patent: Apr. 28, 2026

(54) THRESHOLD-TRIGGERED TRACER PARTICLES

(71) Applicant: PATENTPOOL INNOVATIONS MANAGEMENT GMBH, Munich (DE)

(72) Inventors: Thomas Schimmel, Karlsruhe (DE); Jonathan Berson Kaplan, Karlsruhe (DE); Bastian Rudolph, Karlsruhe (DE)

(73) Assignee: PATENTPOOL INNOVATIONS MANAGEMENT GMBH, Munich (DE)

( * ) Notice: Subject to any disclaimer, the term of this patent is extended or adjusted under 35 U.S.C. 154(b) by 946 days.

(21) Appl. No.: 17/637,585

(22) PCT Filed: Aug. 28, 2020

(86) PCT No.: PCT/EP2020/074096
§ 371 (c)(1),
(2) Date: Feb. 23, 2022

(87) PCT Pub. No.: WO2021/038054
PCT Pub. Date: Mar. 4, 2021

(65) Prior Publication Data
US 2022/0276217 A1     Sep. 1, 2022

(30) Foreign Application Priority Data
Aug. 30, 2019    (EP) ..................................... 19194587

(51) Int. Cl.
G01N 33/24        (2006.01)
G01N 21/17        (2006.01)
(Continued)

(52) U.S. Cl.
CPC ............. G01N 33/24 (2013.01); G01N 21/17 (2013.01); G01N 21/78 (2013.01); G01N 21/80 (2013.01)

(58) Field of Classification Search
CPC ........ G01N 33/24; G01N 21/17; G01N 21/78; G01N 21/80; E21B 47/11; E21B 47/10;
(Continued)

(56) References Cited

U.S. PATENT DOCUMENTS

| | | |
|---|---|---|
| 2012/0142111 A1 | 6/2012 | Tour et al. |
| 2016/0340569 A1 | 11/2016 | Belcher et al. |
| 2017/0000357 A1 | 1/2017 | Gargiulo et al. |

FOREIGN PATENT DOCUMENTS

| | | |
|---|---|---|
| EP | 1862791 A2 | 5/2007 |
| WO | 2019/170856 A1 | 9/2019 |

OTHER PUBLICATIONS

Aznar et al, "Gated Materials for On-Command Replease of Guest Moelcules", Chemical Reviews, vol. 116, No. 2, Jan. 5, 2016, pp. 561-718.*
(Continued)

*Primary Examiner* — Dennis White
(74) *Attorney, Agent, or Firm* — McDonnell Boehnen Hulbert & Berghoff LLP

(57) ABSTRACT

The present invention relates to a threshold-triggered tracer particle having at least a reference function and a reporting function as well as to a composition comprising the same. In addition, the present invention relates to a method of quantifying a porous medium with said composition for detecting physical, chemical or biochemical parameters of the porous medium. Further, the present invention also relates to several uses of said threshold-triggered tracer particles.

13 Claims, 10 Drawing Sheets

Before reaching the threshold

Hull dissolves/separates

Hull becomes permeable

After reaching the threshold

(51) Int. Cl.
    *G01N 21/78*     (2006.01)
    *G01N 21/80*     (2006.01)

(58) Field of Classification Search
    CPC ........ E21B 47/138; E21B 47/06; E21B 47/00;
                                G01K 2211/00; G01K 11/06
    See application file for complete search history.

(56)                         References Cited

OTHER PUBLICATIONS

Aznar et al, "Gated Materials for On-Command Release of Guest Molecules" Chemical Reviews, 2016, 116 (2), 561-718. (Year: 2016).*

King, Lei et al., "Coordination Polymer Coated Mesoporous Silica Nanoparticles for pH-Responsive Drug Release," Advanced Materials (2012), vol. 24, pp. 6433-6437.

Zhu, Yufang et al., "Stimuli-Responsive Controlled Drug Release from a Hollow Mesoporous Silica Sphere/Poly-Electrolyte Multilayer Core-Shell Structure," Angew. Chem. (2005), vol. 117, pp. 5213-5217.

Mignot, Anna et al., "A Top-Down Synthesis Route to Ultrasmall Multifunctional Gd-Based Silica Nanoparticles for Theranostic Applications," Chem. Eur. J. (2013), vol. 19, pp. 6122-6136.

Karmakar, Shyamal, et al., "EGS in Sedimentary Basins: Sensitivity of Early-Flowback Tracer Signals to Induced Fracture Parameters," Energy Procedia (2015), vol. 76, pp. 223-229.

Mornet, Stephane, et al., "The Formation of Supported Lipid Bilayers on Silica Nanoparticles Revealed by Cryoelectron Microscopy," Nano Letters (2005), vol. 5, No. 2, pp. 281-285.

First Examination Report issued in Indian Application No. 202217009265 on Mar. 1, 2024, pp. 1-7. (English translation).

International Preliminary Report on Patentability, from the International Bureau, mailing date of Mar. 10, 2022, for International Application No. PCT/EP2020/074096, pp. 1-9.

Aznar, E., et al., "Gated Materials for On-Command Release of Guest Molecules", Chemical Reviews, Jan. 5, 2016, vol. 116(2), pp. 561-718.

International Search Report from the European Patent Office, mailing date of Nov. 18, 2020, for International Application No. PCT/EP2020/074096, pp. 1-4.

Written Opinion from the International Searching Authority, mailing date of Nov. 18, 2020, for International Application No. PCT/EP2020/074096, pp. 1-7.

Alaskar, M., et al., "Temperature Nanotracers for Fractured Reservoirs Characterization", Journal of Petroleum Science and Engineering, 2015, vol. 127, pp. 212-228.

Lu, C.W., et al., "Bifunctional Magnetic Silica Nanoparticles for Highly Efficient Human Stem Cell Labeling", Nano Letters, 2006, vol. 7(1), pp. 149-154.

Tran, V-L., et al., "Functionalization of Gadolinium Chelates Silica Nanoparticle through Silane Chemistry for Simultaneous MRI/64Cu PET Imaging", Hindawi Contrast Media & Molecular Imaging, Nov. 1, 2018, Article 7938267, pp. 1-11.

Wang, H., et al., "Cu Nanoshells: Effects of Interband Transitions on the Nanoparticle Plasmon Resonance", J. Phys. Chem. B, 2005, vol. 109(39), pp. 18218-18222.

* cited by examiner

Fig. 1
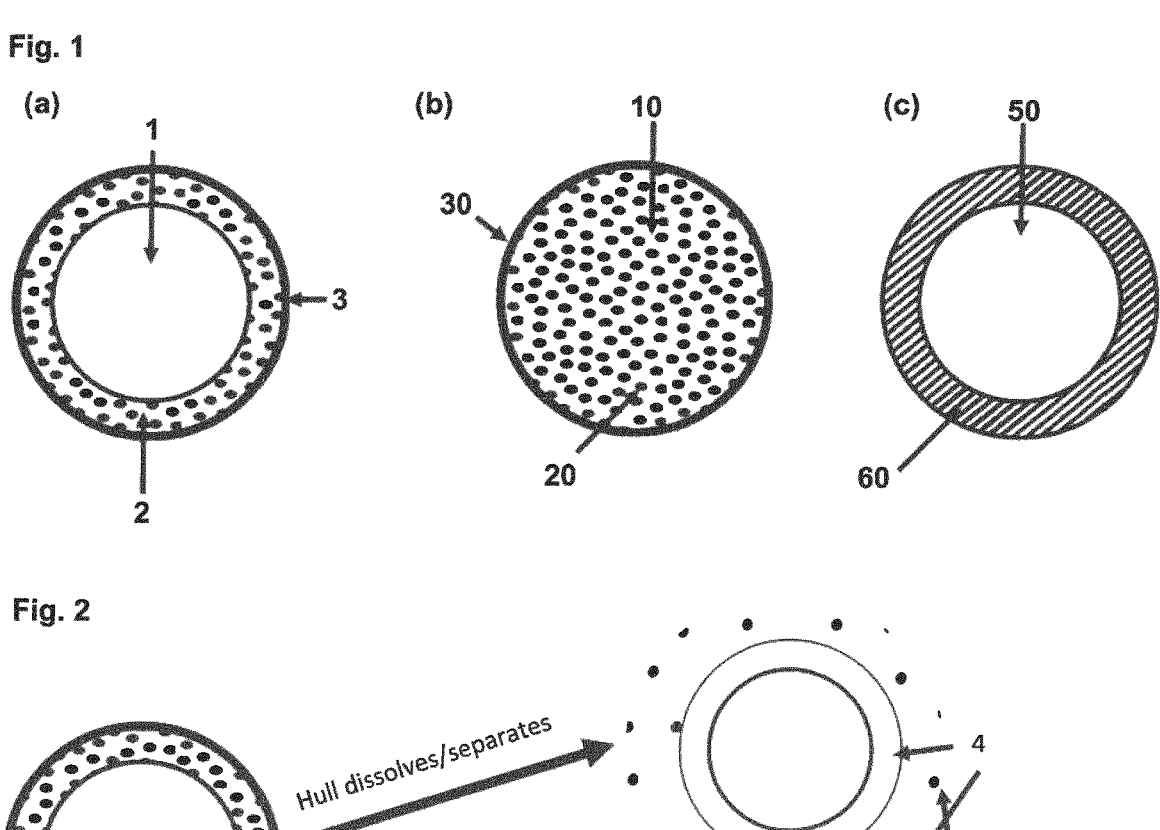
Fig. 2
Hull dissolves/separates
Hull becomes permeable
Before reaching
the threshold
After reaching the threshold
Fig. 3
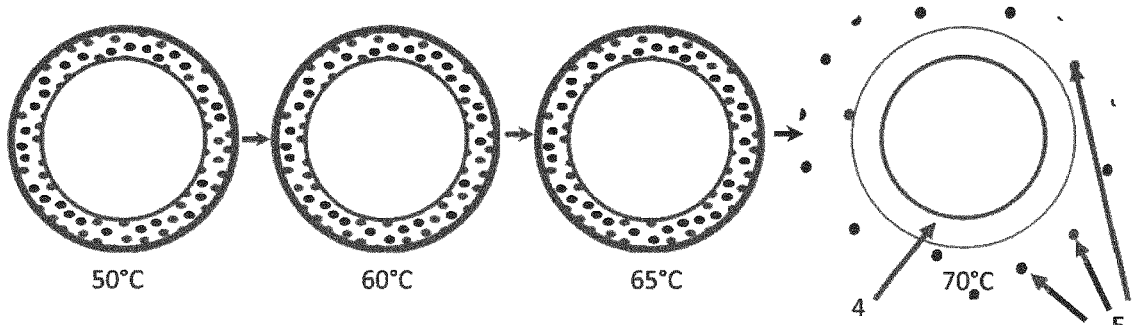
50°C     60°C     65°C     70°C Fig. 4
(a)
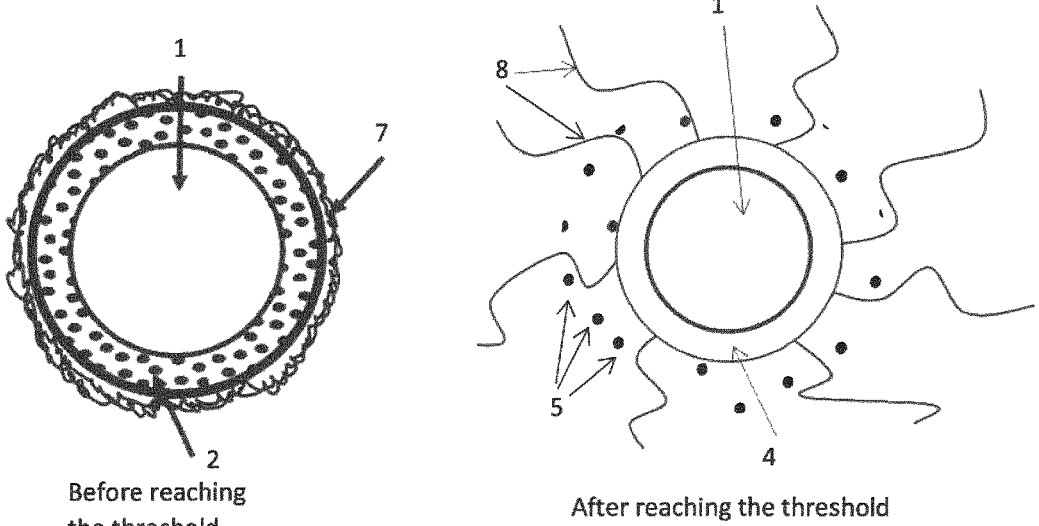
Before reaching
the threshold
After reaching the threshold
(b)
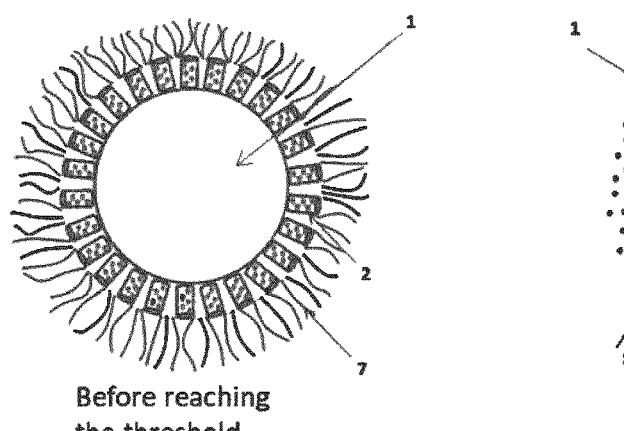
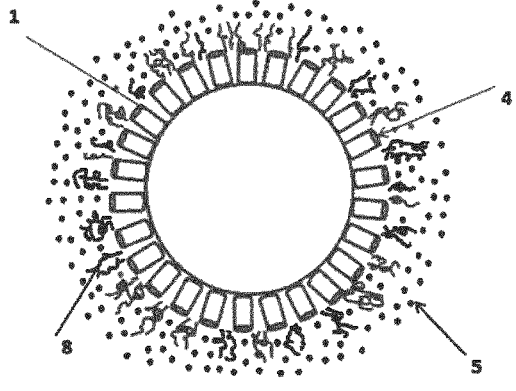
Before reaching
the threshold
After reaching the threshold
(c)
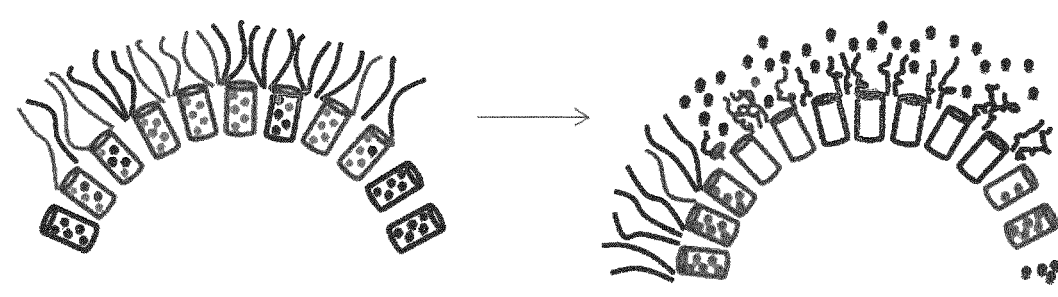

(a)

(b)

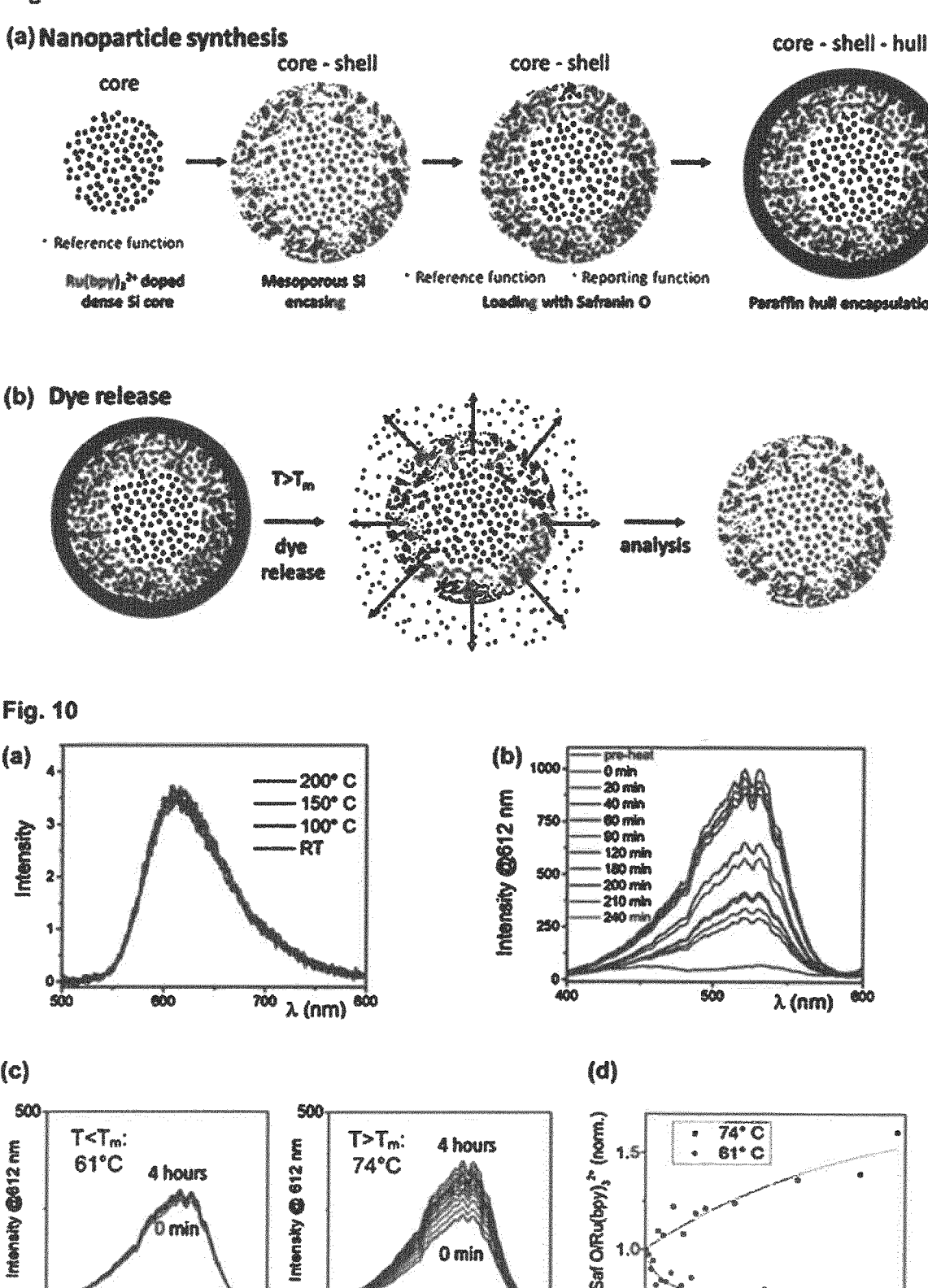

Fig. 9

(a) Nanoparticle synthesis core

- Reference function

Ru(bpy)₃²⁺ doped
dense Si core core - shell

Mesoporous Si
encasing core - shell

- Reference function    - Reporting function
Loading with Safranin O core - shell - hull Paraffin hull encapsulation (b) Dye release

T>Tₘ dye release analysis

Intensity

—— 200° C
—— 150° C
—— 100° C
—— RT

λ (nm)

(b)

Intensity @612 nm pre-heat
0 min
20 min
40 min
60 min
80 min
120 min
180 min
200 min
210 min
240 min λ (nm)

(c)

Intensity @612 nm

T<Tₘ:
61°C          4 hours 0 min

λ (nm)

Intensity @ 612 nm

T>Tₘ:
74°C     4 hours 0 min

λ (nm)

(d)

Saf O/Ru(bpy)₃²⁺ (norm.)

- 74° C
- 61° C

Time (min)

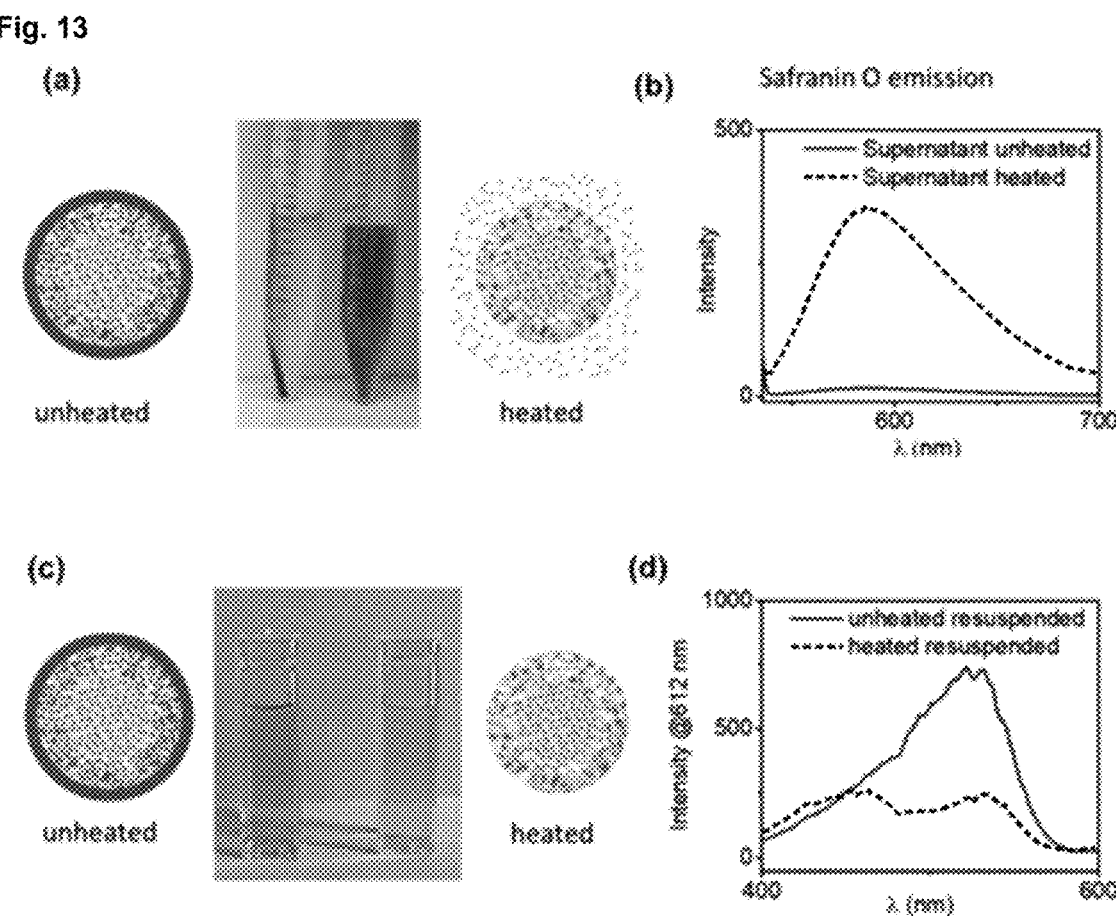

Fig. 14

| yrene | Alexa Fluor® 430 | FAM, 6-isomer | Abberior® STAR 520SXP |
|---|---|---|---|
| Abberior® FLIP 565 | Atto® 430 LS | IBApy 493/503 | Carboxy-rhodamine 6G, 5-isomer |
| Alexa Fluor® 350 | Dy® 430 | Dy® 480 XL | Dy® 521 XL |
| Eterneon™ 350/430 | Dy® 431 | Atto® 488 | Eterneon™ Yellow 530 Azide |
| Eterneon™ 350/455 | Abberior® STAR 440SXP | Abberior® STAR 488 | Alexa Fluor® 532 |
| Dy® 350 | Atto® 465 | IBApy FL | Atto® 532 |
| Dy® 350 XL | Abberior® STAR 470SXP | Abberior® CAGE 500 | Abberior® CAGE 532 |
| Dy® 360 XL | Dy® 478 | Dy® 505 | Dy® 530 |
| Dy® 370 XL | Eterneon™ 480/635 | Dy® 505-X | Atto® Rho6G |
| Dy® 375 XL | Dy® 485 XL | Rhodamine 110X | HEX |
| Dy® 380 XL | Chromeo™ 488 | Dy® 510 XL | Atto® 542 |
| Eterneon™ 384/480 | Oyster® 488 | Dy® 511 XL | Dy® 547P1 |

Fig. 14 - Continued

| Atto® 390 | Dy® 490 | Atto® 514 | Eterneon™ Yellow 550 Azide |
|---|---|---|---|
| Dy® 395 XL | Atto® 490 LS | Eterneon™ Green 515 Azide | Abberior® CAGE 552 |
| Eterneon™ 393/523 | Fluorescein-5-EX | Atto® 520 | Dy® 554 |
| Eterneon™ 394/507 | FAM, 5-isomer | Alexa Fluor® 514 | TAMRA , 5-isomer |
| Dy® 405 | Dy® 495 | Dy® 481 XL | Dy® 555 |
| Alexa Fluor® 405 | Chromeo™ 494 | JOE, 6-isomer | Eterneon™ Yellow 555 Azide |
| Dy® 415 | Alexa Fluor® 488 | TET | Dy® 556 |
| Atto® 425 | Atto® 495 | Dy® 520 XL | Chromeo™ 546 |
| Oyster® 555 | Abberior® CAGE 590 | Abberior® STAR RED | Dy® 681 |
| Oyster® 550 | Eterneon™ Red 600 Azide | Oyster® 647 | Atto® 700 |
| Atto® 550 | Abberior® STAR 600 | Dy® 635 | Alexa Fluor® 700 |
| Alexa Fluor® 555 | Dy® 601 XL | Eterneon™ Red 645 Azide | Dy® 703 |
| Cyanine 3 | Abberior® CAGE 635 | Alexa Fluor® 647 | Dy® 704 |
| TAMRA, 6-isomer | Dy® 605 | Oyster® 650 | Dy® 700 |
| Alexa Fluor® 546 | Atto® Rho13 | Dy® 647 | Dy® 701 |
| Dy® 548 | Atto® 594 | Dy® 652 | Atto® 725 |
| Dy® 547 | Alexa Fluor® 610-X | Dy® 654 | Dy® 734 |
| Dy® 560 | Dy® 610 | Dy® 649P1 | Dy® 730 |
| Dy® 550 | Atto® 610 | Dy® 648 | Dy® 732 |
| Dy® 549P1 | Atto® 620 | Dy® 651 | Dy® 731 |
| Atto® 565 | Dy® 615 | Dy® 650 | Atto® 740 |
| Atto® Rho3B | Atto® Rho14 | Dy® 649 | Dy® 754 |
| Atto® Rho11 | Eterneon™ Red 630 Azide | Atto® 655 | Alexa Fluor® 750 |
| Carboxy-X-rhodamine (ROX), 6-isomer | Atto® 633 | Atto® Oxa12 | Dy® 752 |
| Atto® Rho12 | Alexa Fluor® 633 | Atto® 665 | Cyanine 7 NHS |
| Carboxy-X-rhodamine (ROX), 5-isomer | Abberior® STAR 635 | Alexa Fluor® 660 | Dy® 750 |
| Alexa Fluor® 568 | Abberior® STAR 635P | Methylene Blue (on request) | Dy® 751 |
| Eterneon™ Orange 570 Azide | Dy® 634 | Cyanine 5.5 NHS | Dy® 749P1 |

Fig. 14 - Continued

| Eterneon™ Orange 580 Azide | Dy® 632 | Cyanine 5.5 Amidite | Dy® 778 |
|---|---|---|---|
| Atto® Thio12 | Dy® 631 | Dy® 677 | Dy® 777 |
| Dy® 591 | Dy® 630 | Dy® 678 | Dy® 776 |
| Dy® 590 | Dy® 633 | Dy® 675 | Dy® 780 |
| Abberior® STAR 580 | Atto® 647-N | Dy® 676 | Dy® 781 |
| Sulforhodamine 101 | Dy® 647P1 | Oyster® 680 | Dy® 782 (infrared!) |
| Atto® Rho101 | Dy® 648P1 | Eterneon™ Far Red 680 Azide | Alexa Fluor® 790 |
| Alexa Fluor® 594 | Atto® 647 | Dy® 679P1 | Dy® 800 |
| Cyanine 3.5 NHS | Cyanine 5 NHS | Alexa Fluor® 680 | Atto® 590 |
| Cyanine 3.5 | Cyanine 5 | Atto® 680 | Dy® 636 |
| Dy® 594 | Chromeo™ 642 | Dy® 680 | Dy® 682 |
| Fluorescein | Fluorescein diacetate | Fluorescein sodium salt | Fluorescein isothiocyanate isomer I |
| Fluorescein (free acid) | Fluorescein dilaurate | Fluorescein Phosphoramidite | Fluorescein 5(6)-isothiocyanate |
| Fluorescein isothiocyanate-dextran | Fluorescein diacetate 5-maleimide | Fluorescein o-acrylate | Fluorescein di(β-D-galactopyranoside) |
| Fluorescein-5-thiosemicarbazide | 6-[Fluorescein-5(6)-carboxamido]hexanoic acid | Fluorescein O-methacrylate | 6-[Fluorescein-5(6)-carboxamido]hexanoic acid N-hydroxy-succinimide ester |
| Fluorescein hyaluronic acid | Fluorescein-5-EX N-hydroxysuccinimide ester | Polysucrose 40-fluorescein isothiocyanate conjugate | Fluorescein O,O'-dimethacrylate |
| Fluorescein isothiocyanate isomer I–Celite® | Fluorescein O,O'-diacrylate | Fluorescein diacetate 5(6)-isothiocyanate | Fluorescein diacetate 6-isothiocyanate |
| Fluorescein-O'-acetic acid | Fluorescein α-D-N-acetylneuraminide–Polyacrylamide | Polysucrose -fluorescein isothiocyanate conjugate | Fluorescein galactosamine polyacrylamide |
| 6-Hexachloro-Fluorescein Phosphoramidite | Fluorescein di-(β-D-glucopyranoside) | Fluorescein mono-(N-acetyl-β-D-galactosaminide) | Fluorescein mono-β-D-galactopyranoside |
| Hydroxyphenyl fluorescein | Albumin–fluorescein isothiocyanate conjugate | Iodoacetamidofluorescein | 5-Carboxy-fluorescein diacetate N-succinimidyl ester |
| Biotin – fluorescein conjugate | Aminophenyl fluorescein | FSL-Fluorescein | MTS-4-Fluorescein |
| 5-(Octadecanoylamino)fluorescein | 6-Hexachloro-Fluorescein-Azide | 6-Tetrachloro-Fluorescein Phosphoramidite | 6-Tetrachloro-Fluorescein-Azide |

Fig. 14 - Continued

| | | | |
|---|---|---|---|
| 5-([4,6-Dichloro-triazin-2-yl]-amino)fluorescein hydrochloride | Calcein | Diacetylfluorescein | Chromoionophore XI |
| Fluorescein octadecyl ester | luorescein isothiocyanate–Carboxymethyl–Dextran | Fluorescein isothiocyanate–Diethylaminoethyl–Dextran | 5-Maleimido-fluorescein |
| Mercury dibromo-fluorescein disodium salt | 6-{2-[Bis(2-pyridyl-methyl)amino]ethylamino}fluorescein | {2-[Bis(2-pyridylmethyl)amino]ethylamino}fluorescein diacetate | 6-{2-[Bis(2-pyridylmethyl)amino]ethylamino}fluorescein diacetate |
| Atto 488 maleimide | Atto 550 NHS ester | Atto 488 NHS ester | Atto 655 NHS ester |
| Atto 647N NHS ester | Eosin Y | Erythrosin B | Eosin Y disodium salt |
| Ethyl eosin | 5-Carboxyfluorescein | 5-Carboxyfluorescein N-succinimidyl ester | Rhodamine B octadecyl ester perchlorate |
| 2',7'-Dichloro-fluorescein diacetate | 2',7'-Dichlorofluorescein | Eosin 5-isothiocyanate | Erythrosin B |
| 7-Amino-4-methyl-3-coumarinacetic acid N-succinimidyl ester | 4,5-Diamino-N,N,N',N'-tetraethyl-rhodamine, 4,5-Diamino-rhodamine B | Fluorescent Red Mega 480 | Fluorescent Red Mega 485 NHS-ester |
| Fluorescent Red Mega 520 | Fluorescent Red Mega 520 NHS-ester | Fluorescent Red Mega 500 | Fluorescent Red Mega 480 NHS-ester |
| Atto Rho101 maleimide | Atto 647N azide | Atto 647N iodoacetamide | Atto 647N amine |
| Atto Oxa12 NHS ester | Atto 665 maleimide | Atto Rho101 NHS ester | Atto 488 amine |
| Atto Rho13 maleimide | Atto Rho14 NHS ester | Tris(2,2'-bipyridyl)-dichlororuthenium(II) hexahydrate | Safranin O |
| Tris(2,2'-bipyridine)ruthenium(II) hexafluoro-phosphate | Bis(2,2'-bipyri-dine)-(5-amino-phenanthroline)ruthenium bis(hexafluoro-phosphate) | Coumarine | |

THRESHOLD-TRIGGERED TRACER PARTICLES

CROSS-REFERENCE

This application is a 371 U.S. national phase of PCT/EP2020/074096, filed Aug. 28, 2020, which claims priority from EP 19194587.2, filed Aug. 30, 2019, both which are incorporated by reference in its entirety.

FIELD OF THE INVENTION

The present invention relates to a threshold-triggered tracer particle having a core-shell structure and having at least a reference function and a reporting function as well as to a composition comprising the same. In addition, the present invention relates to a method of quantifying a porous medium with said composition for detecting physical, chemical or biochemical parameters of the porous medium. Further, the present invention also relates to several uses of said threshold-triggered tracer particles.

BACKGROUND OF THE INVENTION

Determination of various conditions and parameters of geological reservoirs, such as temperature, pH or pressure, is of utmost importance, both for the assessment of the profitability of underground usage in terms of geothermal power generation or oil and gas production, as well as for the management and maintenance of running facilities. However, the inaccessibility of such reservoirs, particularly if buried kilometers underground located in dense lithologies, which are impossible to be penetrated by any measurement equipment, make reservoir characterization a complicated task. Beyond the immediate vicinity of wellbores, where the parameters are determined by direct downhole measurement techniques, underground reservoirs are mainly explored by solute tracers. The most basic tracers, some of them used as early as the beginning of the 20$^{th}$ century, were utilized mainly for determining flow path and rates. More elaborate chemical tracers, often referred to as 'smart tracers', detect reservoir conditions, such as temperature, by a chemical transformation that is induced upon experiencing a certain condition within the reservoir. However, chemical tracers have to be used in large quantities in order to be detectable at the recovery point, as just a low fraction of the injected amount is recovered at the exit point due to interaction with and sorption on the reservoir rock. In addition, the reservoir fluids are in general highly mineralized and may mask the signal of the tracer. Moreover, depending on reaction kinetics, most chemical modifications of molecules do not have a sharp threshold and it may be hard to distinguish between e.g. long exposure of the tracer to a moderate temperature and short exposure to a high temperature, as described by S. Karmakar et al., Energy Procedia, 2015 (76), 223-229. A meaningful interpretation of smart tracer experiments requires a priori knowledge of the reservoir parameters such as flow rate, temperature, pH or length of the flow path that is often lacking. Thus, the results based solely on the assessment of the tracer cannot stand on their own.

US 2017/000357 A1, for instance, describes a method for estimating properties of a subterranean formation penetrated by a wellbore in which an injection fluid is introduced into the well and the subterranean formation, wherein the injection fluid comprises a plurality of tracer agents. The tracer agents are either nanoscale gas bubbles, liquid droplets, or solid particles of a specific material. To determine the properties of the subterranean formation, a change in the tracer agents' size and type distribution function is analyzed before and after penetrating the subterranean formation. EP 1 862 791 A2 discloses a method of quantifying a porous membrane using magnetic $Fe_2O_3$ nanoparticles in a fluid having a specific concentration and a calibrated size (mono-dispersed calibrated suspension). A leakage of the porous membrane is detected by measuring the concentration of the mono-dispersed calibrated suspension downstream and upstream of said membrane.

Utilization of nanoparticles in reservoir characterization bears the promise of helping to overcome some of these hardships, while offering many additional possibilities for the development of smart and versatile exploration tools. First and foremost, while being small enough to be able to flow through porous rock layers, nanoparticles can still concentrate a substantial amount of molecules, making detection feasible while using much lower tracer amounts as described e.g. by M. Alaskar et al., Journal of Petroleum Science and Engineering, 2015 (127), 212-228. In this report, temperature-sensitive tracers have been investigated, namely irreversible thermochromic, dye-attached silica and silica-protected DNA particles.

However, an accurate sensing and quantification of parameters, such as pressure, temperature or other physical and/or chemical parameters, when passing through the porous materials, or which physical, chemical and biochemical conditions they were exposed to cannot be reliably achieved. Moreover, analyzing the DNA in the particles requires costly and time-consuming procedures, and cannot be used to perform real-time sampling of the geothermal fluid at the exit point for monitoring purposes.

SUMMARY OF THE INVENTION

Based on this, the object of the invention is to provide a novel tracer system which can be used for characterization of a porous medium, and which enables a reliable and accurate as well as direct and fast way to determine physical, chemical or biochemical parameters of the porous medium.

DESCRIPTION OF THE DRAWINGS

The present invention including preferred embodiments will now be described in more detail along with the accompanying figures. The figures show:

FIG. 1: Part (a) A tracer particle according to the first embodiment having a core-shell structure and a diffusion resistant threshold-triggered hull encapsulating the core-shell structure, part (b) a tracer particle according to the second embodiment having a mesoporous core and a diffusion resistant threshold-triggered hull encapsulating the core, and part (c) a tracer particle according to the second embodiment having a core and a diffusion resistant threshold-triggered hull encapsulating the core, wherein the reporting function is included in the hull.

FIG. 2: The basic functionality of the tracer particle of the present invention in releasing the reporting function once the threshold has been reached.

FIG. 3: The basic principle of the tracer particle of the present invention in releasing the reporting function once a specific threshold temperature has been reached.

FIG. 4: Part (a) A tracer particle according to the first embodiment, wherein the encapsulating hull is realized by a covalently bonded, grafted polymer brush, which upon expanding releases the reporting function, part (b) a tracer particle according to the first embodiment, wherein the encapsulating hull is realized by a covalently bonded, grafted polymer brush, which upon folding releases the reporting function, and part (c) a detailed view of FIG. 4, part (b).

FIG. 9: Part (a) A schematic representation of the stages of the synthesis of the core—shell—hull nanoparticles, and part (b) a schematic representation of the dye release from the shell of the nanoparticles upon exceeding the melting point of the paraffin hull ($T > T_m$), followed by the analysis of particles with a low report/ref ratio after the outer dye had been released.

FIG. 10: Part (a) Fluorescence spectroscopy of the reference signal of the Ru(bpy)$_3^{2+}$ embedded in the nanoparticle core of Reference Example 1, part (b) in-situ time-resolved florescence spectroscopy of the nanoparticle solution of Synthesis Example 1, part (c) in-situ time-resolved fluorescence spectroscopy of the nanoparticle solution of Synthesis Example 1 at different temperatures, and part (d) a graph showing the evolution over time of the signal/ref ratio derived from the fluorescence spectroscopy of the 74° C. (black curve) and 61° C. (red curve) heated solutions shown in FIG. 10, part (c).

FIG. 13: Part (a) A picture of centrifugation tubes containing the pellets and supernatants of solutions of unheated (left) and heated (74° C., right) solutions of nanoparticles of Synthesis Example 1 after centrifugation, part (b) the fluorescence emission signal of the supernatant obtained from the centrifugation tubes, upon excitation at 530 nm, part (c) an image of cuvettes containing solutions of the re-suspended nanoparticles taken from the pellets in the centrifugation tubes, and part (d) fluorescence spectroscopy of the solutions displayed in FIG. 13, part (c), conducted by sweeping the excitation wavelength and measuring the resulting emission at the 612 nm wavelength.

FIG. 14: Gives a non-exhaustive list of fluorescent dyes suitably used in the present invention.

DETAILED DESCRIPTION OF THE INVENTION

Figure 5:
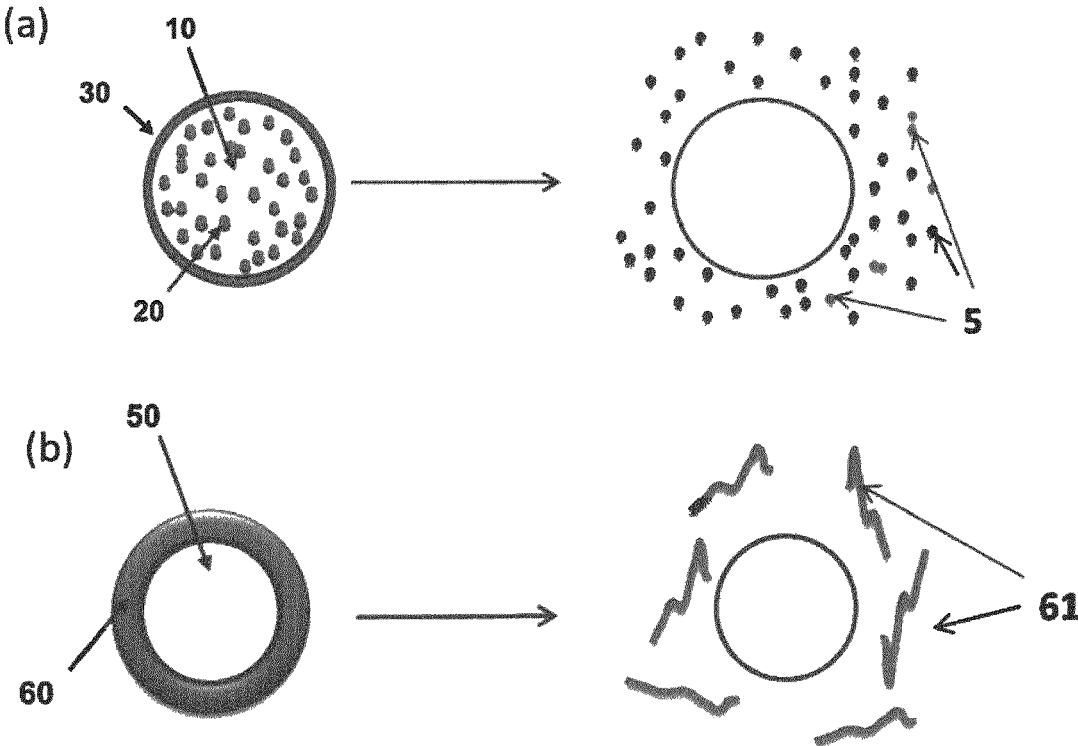
FIG. 5: Parts (a) and (b): The basic functionality of the tracer particle according to the second embodiment in releasing the reporting function once the threshold has been reached.

According to the present invention, the above object is achieved by providing a tracer particle having at least a reference function and a reporting function as characterized herein. The above object is also achieved by a composition comprising the inventive tracer particle as characterized herein as well as by a method of quantifying a porous medium with the composition for detecting physical, chemical or biochemical parameters of the porous medium as characterized herein. Preferred embodiments of the present invention are set out in the dependent claims.

Specifically, the present invention provides a tracer particle having a core-shell structure and having at least a reference function and a reporting function, wherein the particle comprises a core, a mesoporous shell layer and at least one diffusion resistant threshold-triggered hull encapsulating the core-shell structure. According to the present invention, the reference function serves to recognize the particle and as stable signal relative to the variable reporting function, and which is embedded either in the core or in the mesoporous shell layer of the tracer particle. Alternatively, the reference function may be embedded in the core as well as in the mesoporous shell layer of the tracer particle, particularly if more than one reference function is present. The mesoporous shell layer includes the reporting function which changes irreversibly depending on experienced physical, chemical and/or biochemical parameter. Further, according to the present invention, the hull encapsulating the core-shell structure is resistant to the diffusion of the reporting function (diffusion resistant) until a specific threshold in the physical, chemical and/or biochemical parameter has been reached and which is stimuli-responsive triggered by the threshold, upon which the hull dissolves, becomes permeable or temporarily permeable, breaks or separates from the core-shell structure, inducing an irreversible change in the reporting function. Preferably, the hull encapsulating the core-shell structure is also diffusion resistant for molecules and/or ions of a surrounding fluid.

According to the present invention, the mesoporous shell layer is preferably a mesoporous silica layer or a mesoporous polymer layer.

In another aspect, the present invention provides a tracer particle having at least a reference function and a reporting function, wherein the particle comprises an optionally mesoporous core and at least one diffusion resistant threshold-triggered hull encapsulating the core, wherein the reference function serves to recognize the particle and as stable signal relative to the variable reporting function, and which is embedded in the core. The reporting function which changes irreversibly, depending on experienced physical, chemical and/or biochemical parameter, is included in the (mesoporous) core and/or in the hull encapsulating the core, wherein the hull encapsulating the core is resistant to the diffusion of the reporting function (diffusion resistant) until a specific threshold in the physical, chemical and/or biochemical parameter has been reached and which is stimuli-responsive triggered by the threshold, upon which the hull dissolves or separates from the core, inducing an irreversible change in the reporting function. Also, the hull encapsulating the core is preferably also diffusion resistant for molecules of a surrounding fluid.

The present invention further provides a composition comprising at least one or a mixture of at least two different kinds of the tracer particles according to the present invention, and a fluid, wherein the fluid is selected from the group consisting of water, aqueous solutions, oil, an oil-water mixture or emulsion, a generated or natural gas stream, a liquid-gas mixture, and vapor.

Preferably, the composition according to the present invention comprises a mixture of tracer particles having different particle sizes.

In addition, the present invention provides a method of quantifying a porous medium with the composition according to the present invention for detecting physical, chemical or biochemical parameters of the porous medium. In particular, the method comprises the following steps:

introducing the composition into the porous medium, permeating or passing the composition through the porous medium, wherein the at least one reporting function of the tracer particles changes depending on an experienced physical, chemical or biochemical parameter when reaching a threshold value of the parameter to be detected, while the reference function of the tracer particles remains unchanged, and after exiting the porous medium, at least one subsequent analysis of the tracer particles on the physically, chemically or biochemically modified reporting function and the reference function of the tracer particles, wherein the reference function serves for recognizing the tracer particles.

According to a preferred embodiment of the present invention, the reporting function and the reference function are independently selected from the group consisting of a fluorescent marker, a luminescent marker, a plasmonic property marker, or any combination thereof.

Preferably, the core of the tracer particle is a micro- or nanoparticle comprising at least one selected from the group consisting of a metal, a metal oxide, silica, carbon and polymer, especially polystyrene or latex.

Preferably, the diffusion resistant threshold-triggered hull is composed of a fusible material selected from the group consisting of paraffins, lipids, metals, metal alloys, absorbed polymers and grafted polymer brushes, which melts, softens, dissolves or changes structure at a certain temperature or in a certain temperature range.

According to a further preferred embodiment, the diffusion resistant threshold-triggered hull is composed of a polymeric material selected from the group consisting of absorbed polymers, grafted polymer brushes, coordination polymers and polyelectrolytes, which dissolves or becomes permeable when it exceeds or falls below a certain pH or a certain ion concentration.

According to a further preferred embodiment, the diffusion resistant threshold-triggered hull is composed of an oil-soluble substance which dissolves or swells on contact with oil.

In a further preferred embodiment, the tracer particle comprises an additional element showing a time-dependent decay or a time-dependent change of a property. The tracer particle may also comprise an additional magnetic function by comprising magnetic nanoparticles embedded in the core and/or in the mesoporous shell layer, preferably by comprising a ferromagnetic material such as iron-based nanoparticles.

Preferably, at least one of fluorescent molecules, quantum dots and magnetic nanoparticles are embedded in the core as the reference function.

In a further preferred embodiment of the present invention, the above-mentioned tracer particle further comprises a charged species, which is attached to the diffusion resistant threshold-triggered hull or which is integrated into the (mesoporous) core and/or the mesoporous shell layer. Based on said additional charged species, which may be in form of functional groups or in form of a functional layer, the net charge of the tracer particle can be modified in order to minimize adverse phenomena such as sorption inside the porous medium or particle precipitation (agglomeration) in highly salinized, acidic or alkaline fluids. This is achieved by controlling the charge of the particle core or shell or the hull during their formation and/or by integrating into the particles and/or attaching to their surface charged species such as functional groups or functional layers.

The present invention is based on a novel approach for designing tracer particles for the characterization of conditions in a porous medium, which is based on the combination of a number of principles:

The tracer particles have at least one reference function embedded in the core and/or in the mesoporous shell layer and which plays a dual role. On the one hand, the reference function serves to recognize (identify) the particle, i.e. in terms of a signaling function for detection upon recovery, and to determine the concentration of the particles in the medium (quantification). On the other hand, the reference function serves to provide a stable signal that can be compared to the varying signal of the reporting function. According to the present invention, the reference function is embedded in the core and/or in the mesoporous shell layer. The term "embedded" means that the reference function is stably contained in the tracer particle and does not leak out or bleach over time and is protected from degradation, particularly under ambient conditions typical to e.g. geothermal reservoirs, such as temperatures in the range of 200° C. The robust reference function, leak proof and stable, makes measurement analysis straightforward and independent of the need for additional data or simulations.

Further, the tracer particles of the present invention further encompass a stimuli-responsive system, triggered by a sharp threshold and inducing an irreversible change in the reporting function, i.e. a critical threshold value independent on exposure time. In particular, the reporting function which changes depending on any experienced physical, chemical and/or biochemical parameter, may be included in the mesoporous shell layer, or in the mesoporous core, or in the hull encapsulating the core, where it is trapped by the encapsulating hull, which is diffusion resistant until a specific threshold in the physical, chemical and/or biochemical parameter has been reached. Upon reaching the specific threshold, the hull dissolves, becomes permeable or temporarily permeable, breaks or separates from the core, inducing an irreversible change in the reporting function. Here, the term "included" means that the reporting function will be released from the tracer particle or will undergo an irreversible chemical or physical transformation once the hull dissolves, becomes permeable or separates from the core.

The combination of the above principles allows the tracer particles (system) according to the present invention to be used for characterizing a porous medium, enabling a reliable, accurate and highly sensitive (i.e. detection at concentration ranges as low as few nanograms of tracer particles per milliliter) as well as direct and fast way to determine physical, chemical or biochemical parameters of the porous medium.

Besides, when comprising the additional charged species, it is possible to adjust the overall particle charge to minimize adverse phenomena such as sorption inside the porous medium or particle agglomeration, especially in highly salinized, acidic or alkaline fluids. Depending on the nature of the porous medium, the overall charge of the tracer particle can be thus adjusted so as to be alike the charge of the porous medium so as to be repulsive.

As mentioned above, the threshold-triggered tracer particle according to the present invention (hereinafter also referred to as "tracer particle") has at least a reference function and a reporting function. The tracer particle is on the micrometer scale (i.e., in the range of 1 μm to less than 1 mm) or on the nanometer scale (i.e. in the range of 0.5 nm to less than 1 μm). The tracer particle preferably has a diameter (particle size) of from 0.5 nm to 100 μm, more preferably from 5 nm to 10 μm, and particularly from 50 nm to 5 μm. The preferred tracer particles having a diameter of from 0.5 nm to 100 μm will be also referred to as "nanoparticles". Depending on the geological or hydrological analytical question, the particles are used in their pure form or in mixtures as will be described in more detail below.

The diameter of the tracer particles refers to the average particle size, which is determined by Scanning Electron Microscopy (SEM) and especially for the smaller particles by Transmission Electron Microscopy (TEM). In addition, Dynamic Light Scattering can be used to get an estimate of the particle size. For symmetric and spherical particles, the particles size denotes the particle diameter, for asymmetric particles, it denotes the largest dimension of the particle (e.g., the length of stretched particles or tube-shaped particles).

In the synthesis of the particles, the properties of the particle for the dynamic buoyancy in the fluid or the flow or permeation of the porous medium can be influenced and adjusted.

As described above, the tracer particle has a reference function and at least one reporting function for detecting physical, chemical or biochemical parameters. The reference function will be unchanged by the physical, chemical or biochemical parameters and serves to recognize and to determine the concentration of the particle(s) after they have emerged from the porous medium. The reporting function changes as soon as the conditions that the particle experiences as it passes through the medium exceeds or falls below a certain threshold. Such a condition may be a physical quantity, such as temperature, pressure, light, radiation of a certain intensity or wavelength, etc., or a chemical property, such as a specific pH value, ionic strength, concentration of a particular anion or cation, a particular solubility product, or the concentration of a particular chemical species (e.g. a particular molecule, ion, or radical). Preferably, the threshold relates to a specific temperature, pH, or the presence of oil.

According to the present invention, the final analysis of the tracer particle is performed on the reporting function after it has passed through the porous medium, i.e. after the tracer particle flowed through or permeated the porous medium (hereinafter also referred to generally as "passed"), and has exited the porous medium. The term "exit" does not mean that the tracer particle must be spatially separated from the medium in its entirety. Rather, "after exiting the porous medium" is to be understood as meaning that the analysis of the tracer particle (or particle mixture) takes place at a location different from that at which the physical, chemical or biochemical parameters of the medium to be examined should be recorded. Thus, according to the invention, information on the parameters (e.g., in the rock, in the geological formation, in a chemical reactor, or in a human or animal body) is captured in situ by the tracer particles and analyzed ex situ after passing through these locations.

According to the present invention, it is thus possible to investigate areas and places which are otherwise difficult or impossible to access and which are not in visual contact with the observer, preferably in the interior of a geological formation, i.e. not on the surface of the earth, or inside a reactor or a human or animal body.

The tracer particle having at least a reference function and a reporting function may have a core-shell structure, which comprises a core, a mesoporous shell layer and a diffusion resistant threshold-triggered hull encapsulating the core-shell structure as shown in FIG. 1, part (a), for instance (first embodiment). Alternatively, the tracer particle having at least a reference function and a reporting function may comprise a mesoporous core and a diffusion resistant threshold-triggered hull encapsulating the core as shown in FIG. 1, part (b), for instance (second embodiment).

According to the present invention, any measures can be taken for the realization of the reporting function as long as the reporting function is a different entity than the reference function. That means, the reporting function can be distinguished from the reference function of the tracer particle by analytical means. Preferably, the reporting function comprises at least one fluorescent marker, a luminescent marker, or a plasmonic property marker. These can be present individually or in combination.

Also, there are various possibilities for the tracer particles to realize the reference function. However, these variants must meet the following conditions.

(i) They must be clearly identifiable and quantifiable.

(ii) The reference function must be stable under the external conditions that the particles can experience.

Preferably, the reference function is selected from the group consisting of a fluorescent marker, a luminescent marker, a plasmonic property marker, or any combination thereof. In particular, the reference function may be a fluorescent marker, such as fluorescent molecules or quantum dots, or a luminescent marker embedded in the core and optionally in the mesoporous shell layer. Alternatively, the reference function may be realized by metallic nanoparticles showing plasmonic resonances.

Further, the reporting function may be a fluorescent marker, such as fluorescent molecules or quantum dots, or a luminescent marker, which is included either in the mesoporous shell layer (according to the first embodiment), or in the mesoporous core and/or in the hull encapsulating the core (according to the second embodiment). Alternatively, the reporting function may be realized by metallic nanoparticles showing plasmonic resonances or magnetic or ferromagnetic properties. However, the reporting function may also be realized by other molecules, preferably in terms of a cluster, such as metal clusters, transition metal clusters (such as clusters based on copper, silver, gold, iron, cobalt, or nickel), carbon clusters (e.g., fullerenes, graphene) etc., or ionic nanoparticles as well as polymers. As mentioned above, the reporting function is a different entity than the reference function. That means, the reporting function can be distinguished from the reference function of the tracer particle by analytical means.

Fluorescent dyes are preferably used as the reference function as well as the reporting function, since they can be detected at low concentrations with a high signal-to-noise ratio and are less susceptible to false detection as a result of signals emanating from other chemicals in the reservoir fluid. Since the combination of a specific range of excitation and emission wavelengths of a given fluorescent dye is rare, the use of fluorescent dyes in geothermal systems as well as in other porous systems forms an almost unique fingerprint of the tracer particle. Moreover, fluorescence spectroscopy is fast, cheap and simple, which may prove especially advantageous for routine geothermal well real-time monitoring tasks.

Examples of fluorescent dyes that can be used in the present invention include acridines, cyanines, fluorones, fluoresceins, oxazines, phenanthridines, rhodamines, xanthenes, pyrenes, quantum dots, organometalic complex dyes, coumarins, fluorescent proteins, squaranines, naphthalenes, oxadiazoles, anthracenes, arylmethines, and tetrapyrroles. Commercially available fluorescent dyes include CF® dye (Biotium), DRAQ and CyTRAK probes (BioStatus), BODIPY (Invitrogen), Molecular Probes (Invitrogen), Alexa Fluor (Invitrogen), DyLight Fluor (Thermo Scientific, Pierce), Atto and Tracy (Sigma Aldrich), FluoProbes (Interchim), Abberior Dyes (Abberior), DY and MegaStokes Dyes (Dyomics), Sulfo Cy dyes (Cyandye), HiLyte Fluor (AnaSpec), Seta, SeTau and Square Dyes (SETA BioMedicals), Quasar and Cal Fluor dyes (Biosearch Technologies), SureLight Dyes (APC, RPEPerCP, Phycobilisomes)(Columbia Biosciences), APC, APCXL, RPE, BPE (Phyco-Biotech, Greensea, Prozyme, Flogen), Vio Dyes (Miltenyi Biotec). Particular examples for such fluorescent dyes suitably used in the present invention are given in the table shown in FIG. 14. Among those fluorescent dyes, Iluorone dyes, such as rhodamine or rhodamine derivatives, particularly rhodamine B and rhodamine 6G, xanthene dyes, such as fluorescein, as well as phenazine-based dyes or derivatives thereof, such as Safranin O and T, or GFP (Green Fluorescent Protein), or ruthenium bipyridine-based complexes and compounds, such as $Ru(bpy)_3$ (tris(2,2-bipyridyl)dichloro ruthenium (II)), and cadmium selenide quantum dots are particularly preferred.

As mentioned above, a fluorescent dye may be used for the reference function, which is in the following also simply referred to as dye A, as well as for the reporting function, which is in the following also simply referred to as dye B. When selecting the dye A and dye B, however, care must be taken to their compatibility. Detection in a system with two fluorescent emitters is based on the separate determination of the signal-peak-intensity of the two emitters by means of a possible peak-de-convolution. However, since the peaks of fluorescence signals are generally broader, the two signals often overlap. Therefore, when choosing the emitter, care must be taken that the two signals can be separated by either their excitation signal or emission signal.

Referring now to the tracer particle shown in FIG. 1, part (a), according to the first embodiment, the particle comprises, and preferably consists of a core (1), a mesoporous shell layer (2) and a diffusion resistant threshold-triggered hull (3) encapsulating the core-shell structure. The reference function is embedded in the core (1), and the reporting function is included in the mesoporous shell layer (2), which changes once the threshold of the physical, chemical and/or biochemical parameter has been reached (i.e. exceeded or fell below the threshold). In this embodiment, the core of the tracer particle contains the reference function insofar that the reference function is embedded therein. The reference function may be a fluorescent marker, such as fluorescent molecules or quantum dots, or a luminescent marker embedded in the core. Alternatively, the reference function may be realized by metallic nanoparticles showing plasmonic resonances.

Even though not shown in FIG. 1, part (a), the reference function may alternatively or additionally be embedded in the mesoporous shell layer (2).

As mentioned above, according to a preferred embodiment, the fluorescent dye A may be used for the reference function. However, metallic nanoparticles, for instance, are equally suited. In order to realize the reference function, as mentioned above, according to the present invention, several options are conceivable, whereof the following variants 1 to 8 are preferred.

Variant 1 (V1):

In this preferred variant, a fluorescent dye A (see the non-exhaustive list of fluorescent dyes in FIG. 14) is embedded (not covalently bonded) in the matrix of a dense silica nanoparticle during its synthesis, whose particle size is preferably 1 nm to 1000 nm. For this purpose, a version of the Stöber synthesis or a reverse microemulsion synthesis can be used. Embedded in silica, the fluorescent dye (molecule) is particularly stable against external influences and therefore always fulfills the reference function. Thus, in this variant, the core may be also referred to as "reference core". If the reference core is irradiated with light of the wavelength $\lambda_A$, then light of the wavelength $\lambda_A+\delta$ and of the intensity $I_A$ is emitted. The excitation wavelength $\lambda_A$ and the associated wavelength of the emitted light $\lambda_A+\delta$ is specific to the fluorescent dye (molecule), and thus enables accurate identification and, using a calibration curve for the concentration, quantification of the particles. An exemplary synthesis for this variant can be found in Reference Examples 1 and 2 below.

Variant 2 (V2):

Quantum dots A are embedded in the matrix of a silica nanoparticle during its synthesis, whose particle size is preferably 1 nm to 1000 nm. For this purpose, a synthesis similar to variant 1 (V1) can be used. Again, the excitation wavelength $\lambda_A$ and the associated wavelength of the emitted light $\lambda_A+\delta$ is specific to the quantum dots, and thus enables accurate identification and, using a calibration curve for the concentration, quantification of the particles. An exemplary synthesis for this variant is described in Reference Examples 1 and 2 below.

Variant 3 (V3):

Fluorescent ink droplets A are filled into the cavities of a mesoporous silica nanoparticle, whose particle size is preferably 1 nm to 1000 nm, and which is sealed directly afterwards by a dense silica shell. For this purpose, a version of the Stöber synthesis or a reverse microemulsion synthesis can be used, as it is described in Reference Example 3 below.

Variant 4 (V4):

Ink molecules, plasmonic particles or metal nanoparticles are embedded in the matrix of a silica nanoparticle during its synthesis, whose particle size is preferably 1 nm to 1000 nm. For this purpose, a synthesis similar to variant 1 (V1) can be used. When the reference core is irradiated with UV-vis light, the absorption spectrum can identify the core and quantify the number of particles using a concentration calibration curve. An exemplary synthesis for this variant is described in Reference Examples 1 and 2 below.

Variant 5 (V5):

Luminescent ink molecules are embedded in the matrix of a silica nanoparticle during its synthesis, whose particle size is preferably 1 nm to 1000 nm. For this purpose, a version of the Stöber synthesis or a reverse microemulsion synthesis can be used. Using emission spectroscopy, the core can be identified and the number of particles quantified using a concentration calibration curve. An exemplary synthesis for this variant is described in Reference Examples 1 and 2 below.

Variant 6 (V6):

The core is a plasmonic nanoparticle that can be identified and quantified by absorption spectroscopy.

Variant 7 (V7):

The core is a quantum dot, which can be identified and quantified by fluorescence spectroscopy.

Variant 8 (V8):

Luminescent ink molecules are covalently bound in the matrix of a silica nanoparticle during its synthesis, or thereafter using chemical reactions to form stable dye-silica covalent bonds. The particle size is preferably 1 nm to 1000 nm. For this purpose, a version of the Stöber synthesis or a reverse microemulsion synthesis can be used.

Thus, according to the present invention, the core is preferably a micro- or nanoparticle comprising silica, which can be easily and inexpensively produced in large quantities and with a narrow size distribution (dispersity). However, the core may also be composed of other materials.

As another material for the core, polymer particles are preferably used, particularly polystyrene or latex spheres, which are also easy to produce with a narrow size distribution and in spherical form. In addition, carbon micro- and nanoparticles are also preferably used. These are also commercially available.

Another very relevant class of materials are metal particles, such as silver, gold, or copper. Adsorption of, for example, thiols or dithiols, but also of other molecules that alter the plasmonic property, can significantly alter the plasmonic properties of metallic nanoparticles and thus detect them, or use the signal as a reference function. Changes in the plasmonic properties of (i) the intensity of the plasmonic absorption, (ii) the width of the corresponding absorption band, and (iii) the position of the absorption maximum can also be modified by chemical reactions of thiols or dithiols chemisorbed on the surface of the metal nanoparticles. These particles are easy to produce and are readily available commercially.

The particles can have different shapes. However, it is preferred that the core is spherical or is comprised of spherical particles (for example polystyrene, latex or silica spheres).

Besides, the tracer particle according to the present invention (first embodiment) comprises the mesoporous shell layer (2), including the reporting function, and optionally, also the reference function as well as an additional reference function to be described later. According to the present invention, the mesoporous shell layer (2) is preferably a mesoporous silica layer or a mesoporous polymer layer surrounding (covering) the core (1). Preferably, the mesoporous shell layer (2) covers the core (1) in its entirety. The thickness of the mesoporous shell layer (2) is not specifically limited. However, the thickness is preferably 0.4 nm to 1000 nm, whereas a thickness of 1 nm to 200 nm is even more preferred.

The mesoporous shell is a shell made of a material with pores into which other entities such as molecules, clusters of atoms or molecules, fullerenes or particles (preferably nanoparticles) can be (preferably reversibly) included and from which they can be released. Depending on the entities to be included, pore sizes between 0.5 nm and 500 nm are preferred.

According to the present invention, the mesoporous shell layer (2) includes the reporting function. That means, the reporting function is contained in the mesoporous shell layer (2) until the specific threshold in the physical, chemical and/or biochemical parameter has been reached. It is also conceivable that the mesoporous shell layer (2) acts as the reporting function insofar that it is composed of the aforementioned material (fluorescent marker, metallic nanoparticles, clusters, ionic nanoparticles and polymers).

The cavities of the mesoporous shell layer (2) are preferably filled with a fluorescent dye B (see the non-exhaustive list of fluorescent dyes in FIG. 14). This fluorescent dye B is not bound to the pores of the shell layer and would immediately escape into the surrounding medium. To prevent this, the entire particle is encapsulated with the threshold-controlled, diffusion resistant hull (3), which does not transmit a fluorescent molecule or any other reporting function before reaching the threshold value. Only after reaching the specific threshold, the hull dissolves, becomes permeable or temporarily permeable, breaks or separates from the core-shell structure, inducing an irreversible change in the reporting function.

The basic functionality of the tracer particle of the present invention is illustrated in FIG. 2. By means of the reference core (1), an accurate identification and quantification of the existing particles are made at any time. In the initial state, before reaching the respective threshold, the fluorescent dye B is firmly encapsulated in the mesoporous layer (2) around the core (1). This dye B has a specific excitation wavelength $\lambda_B$ and the associated wavelength of the emitted light $\lambda_B+\mu$. If the fluorescence intensity $I_B$ is measured and linked to the quantification by the core (1) (calibration curve), then a concentration-independent intensity $k_{reference}$ can be determined for the initial state. This is the ratio of the signal B to A.

$$k_{reference} = \frac{Signal_{B_{initial\ state}}}{Signal_{A_{initial\ state}}}$$

If it is measured again at a later stage, and the measured value ($k_{measured}$) is equal to $k_{reference}$ ($k_{measured}=k_{reference}$), then it is clearly established that the specific threshold has never been reached.

After reaching the threshold (i.e., by means of a specific temperature, pH, or the presence of oil etc. as mentioned above), the hull (3) becomes permeable (cf. reference sign 6 in FIG. 2), or dissolves, or separates from the core-shell structure, and the fluorescent dye B (5) escapes into the surrounding medium or is irreversibly modified by reacting with it. Concurrently, in response to reaching the threshold, a particle remains which comprises the core, in which reference function is still embedded, and the mesoporous shell layer (4), which does no longer include the reporting function or at least in a decreased amount. Following this, there are two eventualities:

1. The now free fluorescent dye B (5) in the medium and the particle do not move far apart and are measured simultaneously at a later time. This occurs when the process takes place in a sealed container or in a laminar flow with no impurities.

2. The now free fluorescent dye B (5) in the medium and the particle move away from each other and are measured separately at a later time. This occurs when the process takes place in a flowing medium in an environment that favors the separation of a mixture of substances.

In case 1., a stronger signal from fluorescent dye B will be measured, i.e. $I_{B_{before\ threshold}} \neq I_{B_{after\ threshold}}$, while the reference signal of the fluorescent dye A remains unchanged. The increased intensity of the fluorescent dye B is due to the fluorescence quenching effect that occurs when very high concentration fluorophores, such as the fluorescent dye B, exist in the mesoporous shell of the particle. When the fluorescent dye B is released into the surrounding medium, the local concentration decreases and the fluorescence quenching is attenuated. The overall resulting signal from the fluorescent dye B becomes stronger. However, the nominal increase in intensity is not critical. Decisive is the ratio between the reference signal of the fluorescent dye A and the signal of fluorescent dye B, which is also referred to as the ratio of the reporting function to the reference function, in short: "report/ref"

$$k_{measured} = \frac{Signal_B}{Signal_A}.$$

Accordingly, the measurement is not concentration dependent (calibration curve). Thus, in case 1., the measured value ($k_{measured}$) becomes larger than the reference value ($k_{reference}$) ($k_{measured} > k_{reference}$).

In case 2., a pronounced weaker signal from fluorescent dye B will be measured, i.e. $I_{B_{before\ threshold}} \neq I_{B_{after\ threshold}}$, while the reference signal of the fluorescent dye A remains unchanged. This is because the fluorescent dye B is highly diluted or at the same time not in the same location as the particle. Thus, in case 2., the measured value ($k_{measured}$) becomes smaller than the reference value ($k_{reference}$) ($k_{measured} < k_{reference}$).

In view of the above, when measuring the intensity k, the following options occur:

$k_{measured} = k_{reference}$: the specific threshold has never been reached by the tracer particle;

$k_{measured} < k_{reference}$ or $k_{measured} > k_{reference}$: the tracer particle has reached the specific threshold.

As mentioned above, before reaching the respective threshold, the fluorescent dye B or any other reporting function is firmly encapsulated in the mesoporous layer (2) around the core (1). In order to realize the threshold-triggered hull (stimuli-responsivity), according to the present invention, several options are conceivable. In particular, the diffusion resistant threshold-triggered hull is preferably composed of a fusible material selected from the group consisting of paraffins, lipids, metals, metal alloys, absorbed polymers and grafted polymer brushes, which melts, dissolves, swells, changes structure or softens at a certain temperature or in a certain temperature range. As an alternative, the diffusion resistant threshold-triggered hull is preferably composed of a polymeric material selected from the group consisting of absorbed polymers, grafted polymer brushes, coordination polymers and polyelectrolytes, which dissolves or becomes permeable when it exceeds or falls below a certain pH or a certain ion concentration. According to a further preferred embodiment, the diffusion resistant threshold-triggered hull is composed of an oil-soluble substance which dissolves or swells on contact with oil. The above options will be discussed in more detail below.

Paraffin Hull and Temperature Dependency:

In this embodiment, the encapsulating hull is realized with a paraffin layer which, in the solid state before reaching the specific temperature threshold, is diffusion resistant for the fluorescent dye B included within the hull. By choosing the paraffin, it is possible to adjust the specific temperature threshold of the reporting function, since paraffins have a sharp melting point. Only when the temperature threshold is reached, the paraffin hull melts. As a consequence, the fluorescent dye B escapes into the surrounding medium. An exemplary synthesis is described in Reference Example 4.

The above configuration is also illustrated in FIG. 3, showing an example in which the paraffin hull melts at a specific temperature, such as 70° C., for instance. This concept is, however, neither limited to that specific temperature, nor to a paraffin hull, but is applicable to other fusible materials and temperatures.

The paraffin is not specifically limited and can be chosen depending on the specific characteristics to be determined. For instance, the following paraffins summarized in Table 1 along with their melting points (Mp) may be used.

Here, it should also be noted that according to the present invention, in order to provide tracer particles which are soluble in water or other polar solvents, the tracer particles may be mixed with surfactants, amphiphilic molecules or detergents, for instance, e.g., sodium dodecyl sulfate (SDS). It is also conceivable that the surface of the tracer particles is coated (in terms of being modified) with or contains poly-ionic species, such as polyelectrolytes, polymeric salts, as well as dissociable acid groups known in the art. Said measures similarly apply to other hull materials described below.

TABLE 1

| Non-exhaustive list of paraffins | | |
|---|---|---|
| Chemical formula | Name | Mp (° C.) |
| $C_{20}H_{42}$ | eicosane | 36.7 |
| $C_{21}H_{44}$ | henicosane | 40.5 |
| $C_{22}H_{46}$ | Docosane | 43 |
| $C_{23}H_{48}$ | Tricosane | 48-50 |
| $C_{24}H_{50}$ | tetracosane | 49-52 |
| $C_{25}H_{52}$ | pentacosane | 54 |
| $C_{26}H_{54}$ | hexacosane | 56.4 |
| $C_{27}H_{56}$ | heptacosane | 59.5 |
| $C_{28}H_{58}$ | octacosane | 64.5 |
| $C_{29}H_{60}$ | nonacosane | 63.7 |
| $C_{30}H_{62}$ | triacontane | 65.8 |
| $C_{31}H_{64}$ | hentriacontane | 67.9 |
| $C_{32}H_{66}$ | dotriacontane | 65-70 |
| $C_{33}H_{68}$ | tritriacontane | 70-72 |
| $C_{34}H_{70}$ | tetratriacontane | 72.6 |
| $C_{35}H_{72}$ | pentatriacontane | 75 |
| $C_{36}H_{74}$ | hexatriacontane | 74-76 |
| $C_{37}H_{76}$ | heptatriacontane | 77 |
| $C_{38}H_{78}$ | octatriacontane | 79 |
| $C_{39}H_{80}$ | nonatriacontane | 80-82 |
| $C_{40}H_{82}$ | tetracontane | 82 |
| $C_{41}H_{84}$ | hentetracontane | 83-85 |
| $C_{42}H_{86}$ | dotetracontane | 83-86 |
| $C_{43}H_{88}$ | tritetracontane | not available |
| $C_{44}H_{90}$ | tetratetracontane | 85-87 |
| $C_{45}H_{92}$ | pentatetracontane | 86 |
| $C_{46}H_{94}$ | hexatetracontane | 86-89 |
| $C_{47}H_{96}$ | heptatetracontane | 88 |
| $C_{48}H_{98}$ | octatetracontane | 91-93 |
| $C_{49}H_{100}$ | nonatetracontane | 90 |
| $C_{50}H_{102}$ | pentacontane | 91 |
| $C_{60}H_{122}$ | hexacontane | 96-100 |
| $C_{70}H_{142}$ | heptacontane | 105 |

Metal/Metal Alloy and Temperature Dependency:

In this embodiment, the encapsulating hull is realized by a metal or metal alloy layer which, in the solid state before reaching the specific temperature threshold, is diffusion resistant for the fluorescent dye B included within the hull. By choosing the metal and metal alloy, respectively, it is possible to adjust the specific temperature threshold of the reporting function, since metals and metal alloys have a sharp melting point. Only when the temperature threshold is reached, the metal or metal alloy hull melts. As a consequence, the fluorescent dye B escapes into the surrounding medium. An exemplary synthesis is described in Reference Example 5.

The metal/metal alloy is not specifically limited and can be chosen depending on the specific characteristics to be determined. For instance, the following metals and metal alloys summarized in Table 2 along with their melting points (Mp) may be used.

TABLE 2

| Non-exhaustive list of metals/metal alloys | |
|---|---|
| Name | Mp (° C.) |
| Lead | 327.46 |
| Tin | 231.93 |
| Zinc | 419.53 |
| Indium | 156.6 |

TABLE 2-continued

| Non-exhaustive list of metals/metal alloys | |
|---|---|
| Name | Mp (° C.) |
| Aluminum-Copper Alloy | 548 |
| Aluminum-Germanium Alloy | 427 |
| Aluminum-Magnesium Alloy | 437 |
| Aluminum-Zinc Alloy | 382 |
| Amalgam | 178-278 |
| Babbitt Metal | 433-466 |
| Bismuth-Lead Alloy | 125 |
| Field's Metal | 62 |
| Gold-Antimony Alloy | 360 |
| Gold-Bismuth Alloy | 241 |
| Gold-Germanium Alloy | 356 |
| Gold-Lead Alloy | 215 |
| Gold-Silicon Alloy | 363 |
| Gold-Tellurium Alloy | 416 |
| Gold-Thallium Alloy | 131 |
| Gold-Tin Alloy | 278 |
| Lead-Antimony Alloy | 247 |
| Lead-Platinum Alloy | 290 |
| Lead-Tellurium Alloy | 407 |
| Lead-Tin Alloy | 187 |
| Magnesium-Nickel Alloy | 507 |
| Magnesium-Strontium Alloy | 426 |
| Magnesium-Zinc Alloy | 342 |
| Pewter | 240 |
| Rose's Metal | 98 |
| Silver-Lead Alloy | 304 |
| Silver-Lithium Alloy | 145 |
| Silver-Magnesium Alloy | 472 |
| Cerrosafe | 74 |
| Lichtenberg's alloy | 92 |

Adsorbed Polymers and Temperature Dependency:

In this embodiment, the encapsulating hull is realized by adsorbed polymers as pore blockers which, in the solid state before reaching the specific temperature threshold, are diffusion resistant for the fluorescent dye B included within the hull. By choosing the polymer in view of its melting point/glass transition point, it is possible to adjust the specific temperature threshold of the reporting function. When the threshold is reached, the pore blockers dissolve or become porous and permeable, respectively. As a consequence, the fluorescent dye B escapes into the surrounding medium. An exemplary synthesis is described in Reference Example 6.

Lipid-Bilayer and Temperature Dependency:

In this embodiment, the encapsulating hull is realized by a lipid-bilayer which, in the solid state before reaching the specific temperature threshold, is diffusion resistant for the fluorescent dye B included within the hull. By choosing the lipids in view of their melting points, it is possible to adjust the specific temperature threshold of the reporting function. When the threshold is reached, the lipid-bilayer melts. As a consequence, the fluorescent dye B escapes into the surrounding medium. An exemplary synthesis is described in Reference Example 7.

Grafted Polymer Brush and Temperature Dependency:

In this embodiment, the encapsulating hull is realized by a covalently bonded, grafted polymer brush which, in the initial state before reaching the specific temperature threshold, is diffusion resistant for the fluorescent dye B included within the hull. This embodiment is also illustrated in FIG. 4, parts (a)-(c).

By choosing the kind of the grafted polymer brush (7), it is possible to adjust the specific temperature threshold of the reporting function. When the threshold is reached, the grafted polymer brush (8) folds and expands, respectively. As a consequence, the fluorescent dye B (5) escapes into the surrounding medium as shown in FIG. 4, parts (a)-(c). An exemplary synthesis is also described in Reference Example 8.

Adsorbed Polymers and pH Dependency:

In this embodiment, the encapsulating hull is realized by adsorbed polymers as pore blockers which, in the solid state before reaching the specific pH threshold (above or below the specific pH threshold), are diffusion-resistant for the fluorescent dye B included within the hull. By choosing the polymer in view of its pH resistance, it is possible to adjust the specific pH threshold of the reporting function. When the threshold is reached, the pore blockers dissolve or become porous and permeable, respectively. As a consequence, the fluorescent dye B escapes into the surrounding medium. An exemplary synthesis is described in Reference Example 6.

Grafted Polymer Brush and pH Dependency:

In this embodiment, the encapsulating hull is realized by a covalently bonded, grafted polymer brush as pore blocker which, in the initial state before reaching the specific pH threshold (above or below the specific pH threshold), is diffusion-resistant for the fluorescent dye B included within the hull. By choosing the kind of the grafted polymer brush in view of its pH resistance, it is possible to adjust the specific pH threshold of the reporting function. When the threshold is reached, the brush folds and expands, respectively. As a consequence, the fluorescent dye B escapes into the surrounding medium. An exemplary synthesis is described in Reference Example 8.

Grafted Polymer Brush and Oil Detection:

In this embodiment, the encapsulating hull is realized by a covalently bonded, grafted polymer brush as pore blocker which, in the initial state e.g., in an aqueous environment without contact to oil is diffusion-resistant for the fluorescent dye B included within the hull. In the initial state, the polymer brush is stretched and only folds at the interface to oil. When the brush is folded, the fluorescent dye B escapes into the surrounding medium. An exemplary synthesis is described in Reference Example 8.

Polyelectrolytes and pH Dependency:

In this embodiment, the encapsulating hull is realized by an electrostatically adsorbed polyelectrolyte as a pore blocker which, in the initial state (above or below the specific pH threshold) is diffusion resistant for the fluorescent dye B included within the hull. The choice of polyelectrolyte can be used to set the pH threshold for the reporting function. When the threshold is reached, the polyelectrolyte swells, releasing the fluorescent dye B into the surrounding medium. For example, the polyelectrolyte pair sodium polystyrene sulfonate (PSS) and poly(allylamine hydrochloride) (PAH) can encapsulate and later release the encapsulated contents as a reaction to changes in the pH levels. An exemplary synthesis is described in Reference Example 6.

Examples of polymers that can be employed for pH-responsive polyelectrolytes are sodium polystyrene sulfonate (PSS), poly(allylamine hydrochloride) (PAH), poly(methacrylic acid) (PMA), poly(acrylic acid) (PAA), N-isopropylacrylamide (NIPAM) based ionized polymers, polyelectrolytes poly(2-vinylpyridine) (P2VP), and their respective derivatives.

Polyelectrolytes and Salinity:

In this embodiment, the encapsulating hull is realized by an electrostatically adsorbed polyelectrolyte as a pore blocker which, in the initial state (below the specific threshold value of the salt concentration) is diffusion resistant for the fluorescent dye B included within the hull. The choice of polyelectrolyte can be used to set the threshold value of the salt concentration for the reporting function. When the threshold is reached, the polyelectrolyte swells, releasing the fluorescent dye B into the surrounding medium. An exemplary synthesis is described in Reference Example 6.

Coordination Polymers and pH Dependency:

Metal ions are electrostatically bound to a modified surface of the mesoporous shell layer, at which coordination molecules form coordination polymers. In this way, an encapsulating hull is realized which, in the initial state (above or below the specific pH threshold) is diffusion resistant for the fluorescent dye B included within the hull. Via selection of the coordination molecules and metal ions, the pH threshold for the reporting function can be selected. When the threshold is reached, the coordination polymers decompose, releasing the fluorescent dye B into the surrounding medium.

The above embodiments are described with reference to a fluorescent dye B as the reporting function. However, instead of the fluorescent dye B, other fluorescent molecules or quantum dots as well as luminescent markers may also be used. Alternatively, the reporting function may also be realized by metallic nanoparticles showing plasmonic resonances, clusters, ionic nanoparticles and polymers as mentioned above.

According to the present invention, however, not only the above-mentioned conditions relating to a specific temperature, pH, salinity and oil detection can be verified, but also other physical, chemical or biochemical properties can be detected. For instance, a specific pressure might be detected by using a rigid and crushable hull structure in combination with a compressible core. In such an embodiment, the hull will break under a specific pressure, i.e. becomes permeable, and the interior will be exposed to the surrounding medium, which might be an aqueous fluid. If an irreversible chemical reaction now takes place between e.g. a water-sensitive component in the interior of the particle and the water, then this component will change at least one physical or chemical property which can then be used as a reporting function within the meaning of the present invention. This provides evidence that the pressure required to collapse the particle on its way (e.g., through the rock) has been achieved. The threshold pressure, which is the minimum pressure that must be achieved for the particle to break or collapse under external pressure, is very easy to adjust, and tailor-made particles can be produced with different threshold pressures. The pressure that must at least be reached until the particle collapses increases with the shell substance in view of an increased hull thickness and particle diameter. Alternatively, instead of a rigid and crushable hull, the mesoporous shell layer may be crushable, i.e. collapses once the threshold pressure is reached, whereas the hull is made of a compressible material (e.g. paraffin hull).

Also, as mentioned above, according to the present invention, it is also conceivable that besides being released from the tracer particle, the reporting function may undergo an irreversible chemical or physical transformation once the hull dissolves, becomes permeable or separates from the core caused by an interaction with molecules and/or ions of the surrounding medium which may come into contact with the reporting function.

Further, according to the present invention, the tracer particles may preferably be biodegradable (as a whole), or may contain at least one component (i.e. the core, the shell, the fluorescent molecule or the hull), which is biodegradable. In particular, it is preferred that the tracer particles maintain their mechanical and physical properties during practical use, such as at least one day up to 10 years, more preferably at least one day up to several months, but break down into low-weight compounds and non-toxic by-products after their use caused by chemical decay or enzymatic processes resulting from the action of cells. Examples of such biodegradable materials include polyesters, such as polycaprolactone as well as corresponding aromatic and/or aliphatic esters, e.g. polylactic acid, and cellulose-based materials, such as cellulose acetate and cellulose nitrate and derivatives thereof, as well as oligo- and polysaccharides and derivatives thereof. For both the reporting and the reference function, preferably molecules can be chosen from the list of molecules allowed or certified for the use in food, medical applications and drinks. In another implementation of the present invention, the particles dissolve or chemically decay due to long-term contact (preferably between one day and several months) with water or acids or oil.

Preferably, the resulting decay products are oil soluble and thus migrate from the water to the oil, if the reservoir is oil-containing, leaving the water in the long term clean and free of the tracer particles and their decay compounds. This is advantageous in oil reservoir and fracking site investigation, as most of the oil will be finally used for combustion (e.g. in engines or in heating applications), while the remaining water has to be clean.

Moreover, multiple chemical markers can be incorporated into the same tracer particle, i.e. the tracer particle comprises at least two reference functions, enabling the addition of a stable background signal alongside the reporting function. Moreover, multiple chemical markers can be incorporated into the same tracer particle, i.e. the tracer particle comprises at least two reporting functions, enabling the addition of a stable background signal alongside the reporting function. Consequently, each tracer particle can become a complete system with an inherent reference function that is compared to a different, stimuli-responsive, reporting function. Thus, the ratio between the reporting and the reference signals helps overcome the need to know the amount of recovered tracer and reduces the dependency on complicated measurement and simulation of reservoir properties.

Referring now to the tracer particle shown in FIG. 1, part (b), according to the second embodiment, the particle comprises, and preferably consists of a mesoporous core (10) and a diffusion resistant threshold-triggered hull (30) encapsulating the core. The reference function is embedded in the core (10), and the reporting function (shown be reference sign 20), which changes once the threshold of the physical, chemical and/or biochemical parameter has been reached (i.e., exceeded or fell below the threshold), is included in the mesoporous core (10). Even though not shown in FIG. 1, part (b), the reporting function may alternatively or additionally be included in the hull (30) encapsulating the core, as illustrated in FIG. 1, part (c). Here, the particle comprises, and preferably consists of a core (50) and a diffusion resistant threshold-triggered hull (60) encapsulating the core. The reference function is embedded in the core (50). The reporting function, which changes once the threshold of the physical, chemical and/or biochemical parameter has been reached (i.e., exceeded or fell below the threshold), is included in the hull (60) encapsulating the core (50). In these embodiments (according to the second embodiment), except for the aforementioned features, the tracer particle principally corresponds to the tracer particle according to the first embodiment. Thus, the detailed description of the reference function and reporting function as well as the materials of the specific constituents also applies to the second embodiment, and thus is omitted here.

In order to realize the reference function, the following variants are preferred.

Variant 9 (V9):

In this preferred variant, a fluorescent dye A (see the non-exhaustive list of fluorescent dyes in FIG. 14) is embedded in the matrix of a silica nanoparticle during its synthesis, whose particle size is preferably 1 nm to 1000 nm. For this purpose, a version of the Stöber synthesis or a reverse microemulsion synthesis can be used. Embedded in silica, the fluorescent dye (molecule) is particularly stable against external influences and therefore always fulfills the reference function. For this purpose, a synthesis similar to variant 1 (V1) can be used.

Again, the excitation wavelength $\lambda_A$ and the associated wavelength of the emitted light $\lambda_A+\delta$ is specific to the fluorescent dye (molecule), and thus enables accurate identification and, using a calibration curve for the concentration, quantification of the particles.

Variant 10 (V10):

Instead of a fluorescent dye, plasmonic particles or metal nanoparticles are embedded in the matrix of a silica nanoparticle during its synthesis, whose particle size is preferably 1 nm to 1000 nm. For this purpose, a synthesis similar to variant 1 (V1) can be used. When the reference core is irradiated with UV-vis light, the absorption spectrum can identify the core and quantify the number of particles using a concentration calibration curve.

Variant 11 (V11):

Luminescent ink molecules are embedded in the matrix of a silica nanoparticle during its synthesis, whose particle size is preferably 10 nm to 1000 nm. For this purpose, a version of the Stöber synthesis or a reverse microemulsion synthesis can be used. Using emission spectroscopy, the core can be identified and the number of particles quantified using a concentration calibration curve.

Besides, according to the second embodiment, the mesoporous core (10) may include the reporting function. In particular, the cavities of the mesoporous core (10) are preferably filled with a fluorescent dye B (see the non-exhaustive list of fluorescent dyes in FIG. 14). This fluorescent dye B is not bound to the pores of the core and would immediately escape into the surrounding medium. To prevent this, the core (10) is encapsulated with the threshold-controlled, diffusion resistant hull (30), which does not transmit a fluorescent molecule before reaching the threshold value. Only after reaching the specific threshold, the hull dissolves or separates from the core (10), inducing an irreversible change in the reporting function.

The basic functionality of the tracer particle according to the second embodiment corresponds to that of the first embodiment and is illustrated in FIG. 5, part (a). In the initial state, before reaching the respective threshold, the fluorescent dye B (20) or any other reporting function is firmly encapsulated in the mesoporous core (10). After reaching the threshold (i.e. by means of a specific temperature, pH, or the presence of oil etc. as mentioned above), the hull (30) dissolves or separates from the core (10), and the fluorescent dye B (5) escapes into the surrounding medium, leaving behind the core (10) still containing the reference function.

As mentioned above, this dye B has a specific excitation wavelength $\lambda_B$ and the associated wavelength of the emitted light $\lambda_B+\mu$. By applying the above-mentioned methodology, it can be evaluated as to whether the specific threshold has been reached.

Similarly to the first embodiment, the diffusion resistant threshold-triggered hull is preferably composed of a fusible material selected from the group consisting of paraffins, lipids, metals, metal alloys, absorbed polymers and grafted polymer brushes, which melts, dissolves, changes structure, or softens at a certain temperature or in a certain temperature range. As an alternative, the diffusion resistant threshold-triggered hull is preferably composed of a polymeric material selected from the group consisting of absorbed polymers, grafted polymer brushes, coordination polymers and polyelectrolytes, which dissolves or becomes permeable when it exceeds or falls below a certain pH or a certain ion concentration. According to a further preferred embodiment, the diffusion resistant threshold-triggered hull is composed of an oil-soluble substance which dissolves on contact with oil. The above options have been discussed in detail above.

As shown in FIG. 1, part (c), it is also conceivable that the reporting function is included in the hull (60) encapsulating the core (50). According to this embodiment, a fluorescent dye A (see the non-exhaustive list of fluorescent dyes in FIG. 14) or any other reference function, such as metallic nanoparticles, is embedded in the matrix of a silica nanoparticle. This serves as the reference function and can be precisely identified at any time due to its specific excitation and emission wavelength. In addition, by measuring the intensity of the emission, a calculation of the concentration of particles in the medium can be achieved as described above.

The core (50) is encapsulated by a fluorescent lipid or fluorescent polymer in terms of a threshold-controlled, diffusion resistant hull (60). This fluorescent lipid or fluorescent polymer is used as reporting function. As long as the threshold is not reached, the hull (60) stably remains on the silica nanoparticle (50). As shown in FIG. 5, part (b), only after reaching the specific threshold, the hull dissolves or separates from the core, inducing an irreversible change in the reporting function due to the separation of the hull fragments (61).

The fluorescent polymer is not specifically limited and can be chosen depending on the specific characteristics to be determined. For instance, the following polymers in Table 3 along with their melting points (Mp) or glass transition points (Tg), respectively (if available), may be used.

TABLE 3

| Non-exhaustive list of fluorescent polymers | |
| --- | --- |
| Name | Mp (° C.) |
| Poly(9-anthracenylmethyl acrylate) | 205-215 |
| Poly(9-anthracenylmethyl methacrylate) | 195 |
| Poly(3,3',4,4'-benzophenonetetracarboxylic dianhydride-alt-Acridine Yellow G) | >400 |
| Poly(3,3',4,4'-benzophenonetetracarboxylic dianhydride-alt-3,6-diaminoacridine hemisulfate) | >400 |
| Poly(ethylene oxide), 6-arm, anthracene terminated (average Mn ~10,000) | 48-53 |
| Poly(fluorescein O-acrylate) | |
| Poly(fluorescein isothiocyanate allylamine hydrochloride) | |
| Poly(allylamine hydrochloride):Fluorescein isothiocyanate 50:1 | |
| Poly(fluorescein isothiocyanate allylamine hydrochloride) | |
| Poly(allylamine hydrochloride):Fluorescein isothiocyanate 50:1 | |
| Poly(fluorescein O-methacrylate) | |
| Poly[(4,4'-hexafluoroisopropylidene)diphthalic anhydride-alt-Acridine Yellow G] | >400 |
| Poly[(4,4'-hexafluoroisopropylidene)diphthalic anhydride-alt-3,6-diaminoacridine hemisulfate] | >400 |
| Poly[(methyl methacrylate)-co-(9-anthracenylmethyl methacrylate)] | Tg 103 |
| Poly[methyl methacrylate-co-(fluorescein O-acrylate)] | Tg 156 |
| Poly[(methyl methacrylate)-co-(fluorescein O-methacrylate)] | Tg 148 |

TABLE 3-continued

| Non-exhaustive list of fluorescent polymers | |
| --- | --- |
| Name | Mp (° C.) |
| Poly[(methylmethacrylate)-co-(2-naphthyl methacrylate)] | Tg 102 |
| Poly[(methyl methacrylate)-co-(N-(1-naphthyl)-N-phenylacrylamide)] | Tg 67 |
| Poly[(methyl methacrylate)-co-(7-(4-trifluoromethyl)coumarin acrylamide)] | |
| Poly[(methyl methacrylate)-co-(7-(4-trifluoromethyl)coumarin methacrylamide)] | |
| Poly(2-naphthyl acrylate) | Tg 59 |
| Poly(2-naphthyl methacrylate) | Tg 73.7 |
| Poly[N-(1-naphthyl)-N-phenylacrylamide] | |
| Poly[N-(1-naphthyl)-N-phenylmethacrylamide] | |
| Poly(pyromellitic dianhydride-alt-acridine yellow G) | >400 |
| Poly(pyromellitic dianhydride-alt-3,6-diaminoacridine hemisulfate) | >400 |
| Poly(pyromellitic dianhydride-alt-ethidium bromide) | >360 |
| Poly(pyromellitic dianhydride-co-thionin) | >400 |
| Poly(2-vinylnaphthalene) (average Mn ~5,000) | Tg 130 |

However, the diffusion resistant threshold-triggered hull may also be composed of any other fusible material mentioned above, which melts or dissolves at a certain temperature or in a certain temperature range, and which preferably includes a fluorescent dye B. Also, the diffusion resistant threshold-triggered hull can be composed of a polymeric material selected from the group consisting of absorbed polymers, grafted polymer brushes, coordination polymers and polyelectrolytes including a fluorescent dye B, which dissolves when it exceeds or falls below a certain pH or a certain ion concentration. In addition, the diffusion resistant threshold-triggered hull may be composed of an oil-soluble substance including a fluorescent dye B, which dissolves or swells on contact with oil.

According to the present invention, the tracer particle may further comprise a cationic, anionic or otherwise charged species, which is attached to the diffusion resistant threshold-triggered hull or which is integrated into the (mesoporous) core and/or the mesoporous shell layer. As mentioned above, based on such an additional charged species, it is possible to adjust the overall particle charge to minimize adverse phenomena such as sorption inside the porous medium or particle agglomeration, especially in highly salinized, acidic or alkaline fluids. Depending on the nature of the porous medium, the overall charge of the tracer particle can be thus adjusted so as to be alike the charge of the porous medium so as to be repulsive.

According to the present invention, the tracer particle may further have an additional function in addition to the reference and reporting function. For these trifunctional particles, nanoparticles having the aforementioned sizes (diameters) are also preferred. This additional function can be a timer function that allows the time of the tracer particle from the injection to the detection after leaving the porous medium to be determined on the basis of a time-dependent decay or a time-dependent change of a property. Radioactive decay is just one example. Chemical decay, the conversion of one isomer to another more stable isomer, or oxidation with loss of the fluorescent property are further examples.

This additional function can also be a magnetic function. In particular, trifunctional micro- and nanoparticles whose third function is based on magnetic properties, preferably ferromagnetism, are also preferred according to the present invention. This can be realized, for example, in that the tracer particle also contains magnetic inclusions in addition to the reporting function and the reference function. Preferably, the tracer particle comprises iron-based nanoparticles embedded in the core and/or in the mesoporous shell layer. This facilitates the concentration and removal of the tracer particles from the fluid at the exit point using magnets and magnetic fields. For example, after leaving the porous medium, the fluid may flow through a grid or mesh that has magnetic properties and attracts and holds the particles. However, the tracer particle may comprise any other ferromagnetic material embedded in the core and/or in the mesoporous shell layer. For instance, instead of iron-based nanoparticles, ferromagnetic nanoparticles based e.g., on nickel, copper, ruthenium, gadolinium, terbium, dysprosium, alloys of said elements as well as corresponding oxides, such as chromium dioxide, europium oxide etc., known to have ferromagnetic properties may be mentioned. An exemplary synthesis is described in Reference Example 9.

As mentioned above, according to the present invention, it is preferable that at least one of fluorescent molecules, quantum dots and magnetic nanoparticles are embedded in the core as the reference function.

In particular, in a preferred embodiment, the tracer particle has the following configuration:

the core is a nanoparticle comprising silica, carbon, or polymer (especially polystyrene or latex), in which the reference function is embedded in terms of a fluorescent dye A (see the non-exhaustive list of fluorescent dyes in FIG. 14);

the mesoporous shell layer is a mesoporous silica layer, which includes the reporting function in terms of a fluorescent dye B (see the non-exhaustive list of fluorescent dyes in FIG. 14); and the hull encapsulating the core-shell structure is composed of either a fusible material selected from the group consisting of paraffins, lipids, metals and metal alloys, or a polymeric material which dissolves or becomes permeable when it exceeds or falls below a certain pH or a certain ion concentration, or an oil-soluble substance which dissolves on contact with oil.

In a further preferred embodiment, the tracer particle has the following configuration:

the core is a mesoporous silica nanoparticle, in which the reference function is embedded in terms of a fluorescent dye A (see the non-exhaustive list of fluorescent dyes in FIG. 14);

the mesoporous silica nanoparticle further includes the reporting function in terms of a fluorescent dye B (see the non-exhaustive list of fluorescent dyes in FIG. 14); and the hull encapsulating the core is composed of either a fusible material selected from the group consisting of paraffins, lipids, metals and metal alloys, or a polymeric material which dissolves or becomes permeable when it exceeds or falls below a certain pH or a certain ion concentration, or an oil-soluble substance which dissolves on contact with oil.

Further, a preferred identification of the tracer particle is given by the simultaneous use of two fluorescent markers in a particle for recognition (double recognition function). Thus, the tracer particle is always recognizable as a particle of a certain injection lot. If different labeled particles are introduced at different times or at different locations, one can—if necessary even years later—know where these particles come from. If these particles now escape again, they carry information about the experienced environmental conditions during their passage or residence time in the rock, for instance. Such particles can be introduced billions of times. By the combination of particles, which are changed by different environmental conditions (threshold of the temperature, the pressure etc.), different experienced environmental conditions can be interrogated at the same time. Thus, an analysis is possible that, for example, 70% of the particles encountered temperatures above 250° C. and 20% of the particles encountered temperatures above 300° C. and further 44% of the particles have met pH values below 4.5.

Figure 6:
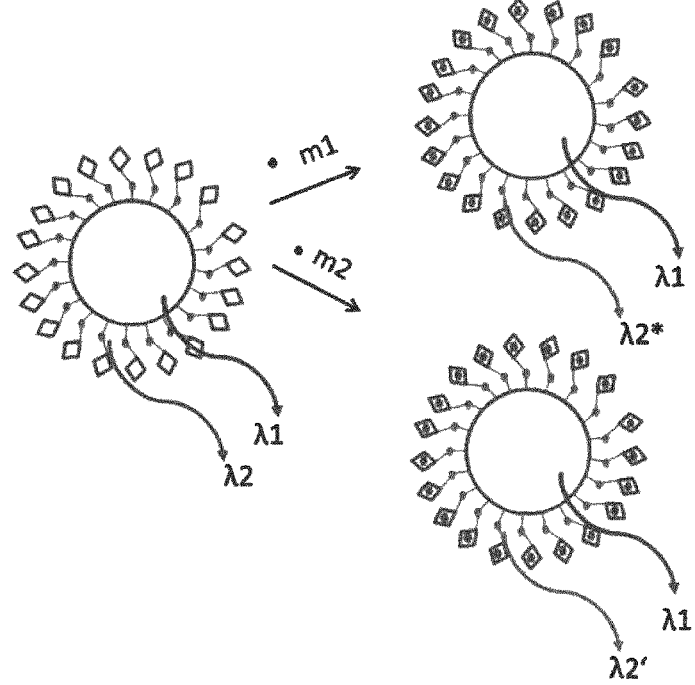
FIG. 6: A tracer particle which comprises a reporting function which reacts differently to different stimuli.

However, it is also possible that the tracer particle according to the present invention comprises a reporting function which reacts differently to different stimuli. An example of this is a micro- or nanoparticle with ion chelating complexes on its surface, which are conjugated to a fluorophore with an emission wavelength $\lambda_2$. When the chelating complex irreversibly chelates a metal ion, the fluorescence signal of the conjugated fluorophore shifts. The shift in the fluorescence signal depends on the chelated metal ion, so different chelated ions m1 or m2 will induce a different shift from $\lambda_2$ to $\lambda_2$· or to $\lambda_{2'}$, respectively. This embodiment is illustrated in FIG. 6. An exemplary synthesis of modifying silica nanoparticles with chelating agents is described in Reference Example 10.

According to a preferred embodiment of the present invention, the reporting function of the tracer particles changes when the threshold value is exceeded or fell below a sharp value or a narrow value range, for example a melting temperature of the fluorescent dye-stained paraffin hull of ±10° C., preferably ±5° C., more preferably ±3° C.

It is also preferred that the tracer particle according to the present invention comprises more than two shells (hulls) apart from the core. In particular, the tracer particle may comprise multiple diffusion resistant threshold-triggered hulls encapsulating the core in terms of concentric shells. An example is the combination of an outer hull which is lost when it exceeds a certain temperature (due to the specific melting point of the hull material, for instance) with a second inner hull which is dissolved or becomes permeable when a specific pH is reached. The first threshold relating to the temperature triggers that a first fluorescent dye having a first fluorescence wavelength as reporting function will be released to the surrounding medium. In addition, if the surrounding medium falls below or exceeds a specific pH value, the inner hull dissolves or becomes permeable, thereby triggering that the second fluorescent dye having a second fluorescence wavelength as reporting function will be released to the surrounding medium.

In a further aspect, the present invention provides a composition comprising at least one or a mixture of at least two different kinds of the tracer particles according to the present invention, and a fluid. In general, the fluid passing through the porous medium may not only be a liquid, but may also be a gas, a gel or a liquid-gas mixture, an emulsion, a mist (liquid droplets are carried with a gas), or an aerosol. The fluid may thus be water, aqueous solutions, oil, an oil-water mixture or emulsion, a generated or natural gas stream, a liquid-gas mixture, and vapor.

The tracer particles, in particular nanoparticles, with the reference and reporting function can be located in each component of such mixed fluids. They may be in one component or in more than one component, for example both in the liquid droplets and in the vapor phase of a mist, or in only one of them.

The fluid may also contain additives and/or detergents mentioned above. Preferably, the gas stream consists of air, industrial gases or noble gases or mixtures thereof.

Principally, in addition to the reporting function and the associated information on threshold values, all tracer particles according to the present invention also provide the same information via their reference function as conventional tracers on the flow behavior of a media, e.g. in underground currents. Thus, the composition according to the present invention preferably comprises a mixture of tracer particles having different particle sizes. When using different sizes with different reference signals, information about the duration of different sized tracer particles in different layers and pores can be obtained.

According to the present invention, it is also possible to combine various tracer particles which are sensitive to different thresholds, such as different temperatures. For example, the use of 10 different tracer particles whose hulls melt at 10° C., 20° C., 30° C., 40° C., 50° C., 60° C., 70° C., 80° C., 90° C. and 100° C. may be mentioned, in which each tracer particle contains a different reference function. This allows detailed conclusions to be drawn in 10-degree increments, which temperatures were exceeded and which did not and how many percent of the particles experienced which temperature exceeded on their way through the porous medium and thus, for example, lost their hull in the embodiment mentioned above.

Figure 7:
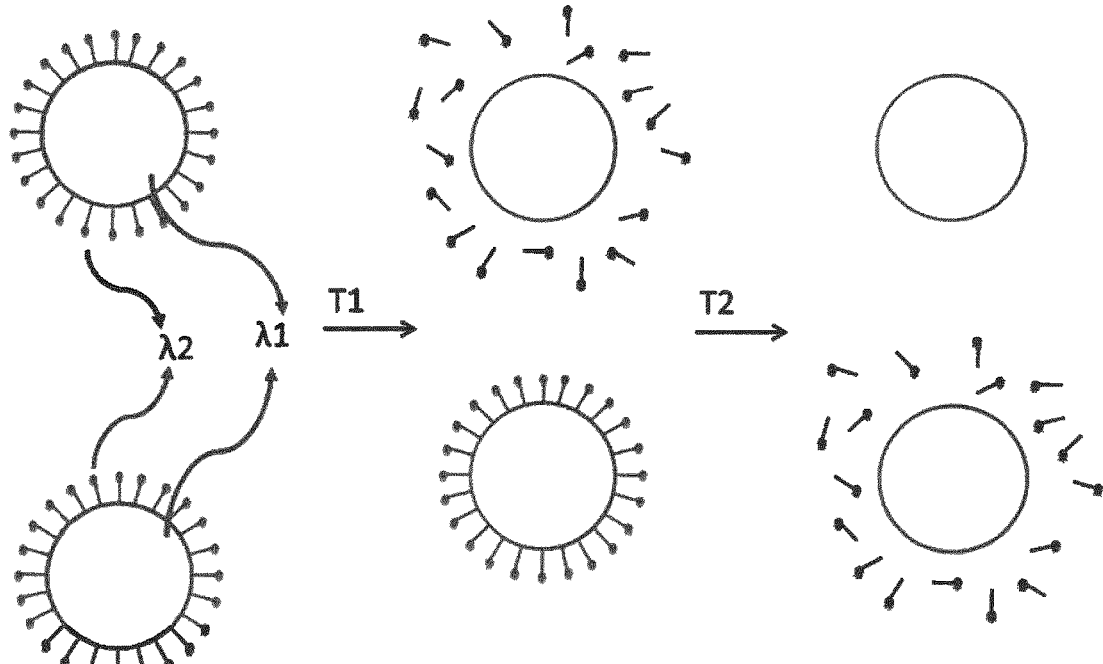
FIG. 7: A combination of different kinds of tracer particles for the evaluation of different temperature thresholds.

Another embodiment is that different tracer particles which are sensitive to different thresholds, such as different melting points of the hull (i.e. a first temperature T1 and a second temperature T2), are introduced simultaneously or sequentially and the flow/permeation is observed or analyzed by time-dependent chromatographic analysis. The combination of these different kinds of tracer particles is also illustrated in FIG. 7. In this case, the reference function is the same for all particle types. However, the reporting function will be released at different thresholds. In an analogous manner, it is of course also possible to analyze different properties (such as pH value, oxygen exposure etc.) simultaneously or sequentially.

Thus, in a further aspect, the present invention also relates to the use of the tracer particles according to the present invention for the characterization of rocks, rock layers and/or porous materials or layers of this porous material, in the geological examination of rocks, rock layers and/or porous materials or layers of this porous material, in hydrology, aquatic exploration, reservoir exploration, reservoir monitoring, oil detection, fracking, geothermal, leak detection, monitoring of chemical, biological and/or biotechnological reactors, water tanks, reservoirs and water supply systems, or medical in vivo procedures.

Hereinafter, the method of characterizing a porous medium with the composition according to the present invention for detecting physical, chemical or biochemical parameters of the porous medium is described in more detail. The method according to the present invention comprises the following steps:

introducing the composition into the porous medium, permeating or passing the composition through the porous medium, wherein the at least one reporting function of the tracer particles changes depending on an experienced physical, chemical or biochemical parameter when reaching a threshold value of the parameter to be detected, while the reference function of the tracer particles remains unchanged, and after exiting the porous medium, at least one subsequent analysis of the tracer particles on the physically, chemically or biochemically modified reporting function and the reference function of the tracer particles, wherein the reference function serves for recognizing the tracer particles.

Figure 8:
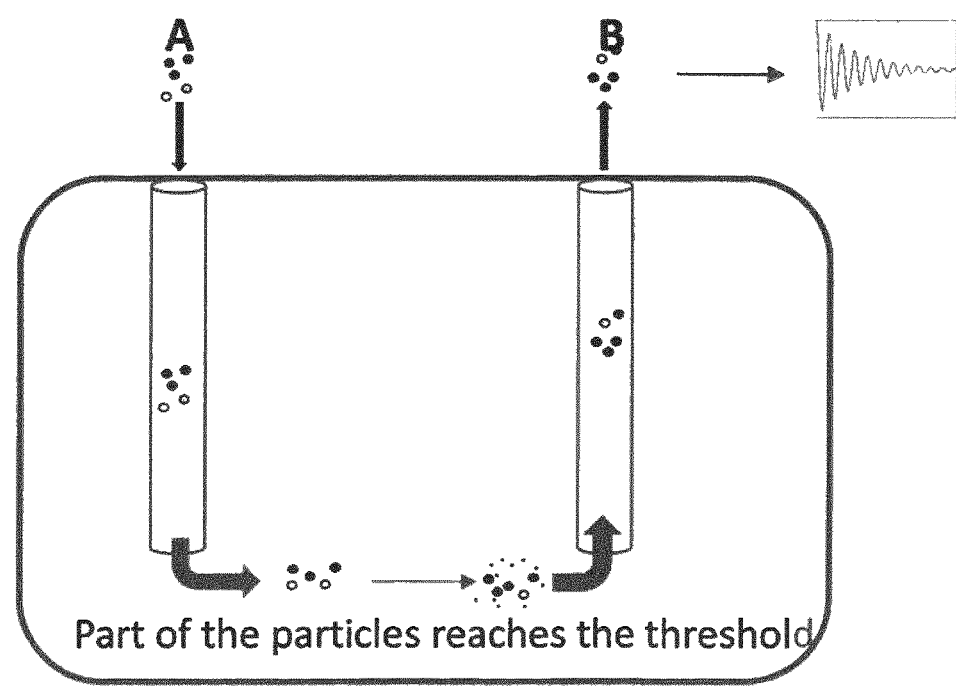
FIG. 8: The principle of the method of quantifying a porous medium with the composition according to the present invention.

For instance, the method may be applied for the characterization of rocks, rock layers and/or porous materials or layers of this porous material in the geological examination of rocks, rock layers and/or porous materials or layers of this porous material. Rock refers to a solid, naturally occurring, usually microscopically heterogeneous combination of minerals, rock fragments, glasses or residues of organisms. The mixing ratio of these constituents to one another is largely constant, so that a rock, in spite of its detailed composition, acts uniformly in the case of free-eyed viewing. A detectable property change is caused by certain physical, chemical or biochemical environmental conditions of the material to be examined. If the tracer particle encounters such ambient conditions on its way through the porous medium or rock (for example: to a temperature of at least 80° C.), then the tracer particle is irreversibly changed in the reporting function, which, after leaving the porous medium or rock, is detectable. This property change of the tracer particle is now detected after exiting the porous medium, as it is illustrated in FIG. 8.

The detection is done, for example, in the following manner. At the exit point of the fluid, samples are taken and the fluid is examined with the tracer particles. It is also possible to enrich the particles beforehand, e.g. by centrifugation or ultracentrifugation, magnetic collection or by sedimentation. Separately or in combination with the sampling, the properties can be examined in real time in the passing liquid, for example through glass windows in the flow cell of a spectrometer through which the fluid flows. The change in the properties of the tracer particles may have very different properties. This may in particular be the absorption of electromagnetic radiation, such as light, ultraviolet radiation or infrared radiation or microwave radiation. But it may also be a change in the magnetic properties, such as ferromagnetic or superparamagnetic particles and nanoparticles, which can be done, for example, by oxidative change by the action of oxygen. However, it may also be a change in the dielectric properties, which can likewise be effected by oxidative change by the action of oxygen, but also by other chemical alteration of the tracer particle or its surface or of the relevant molecule.

Depending on the type of tracer particles used, changes in the particle properties can also be detected by NMR and ESR (nuclear magnetic resonance or electron spin resonance). Likewise, the property changes can be detected by means of ENDOR (Electron Nuclear Double Resonance) by magnetic resonance.

However, as mentioned above, it is preferred that the reporting function is realized by a fluorescent marker, which results in a change in the fluorescence properties, including the following options: change in the fluorescence intensity or change in the fluorescence wavelength or appearance of new fluorescence or appearance of the fluorescence at a different excitation wavelength than before. The latter is particularly preferred for the detection described below. At a certain excitation wavelength, after flowing through the porous medium, fluorescence that did not exist before flowing through the porous medium occurs, or only at a lower intensity. Alternatively, at a certain excitation wavelength occurs before flowing through the porous medium to a fluorescence on which no longer exists after flowing through the porous medium, or only with lower intensity.

After the tracer particles have passed through the porous medium, they must be examined for the change in the reporting function. In the flow method or in-situ method, the fluid with the tracer particles passes a sensor or a measuring device which detects both the reporting function and the reference function. This can be done, for example, by flowing through an optical flow cell in a spectrometer or fluorescence spectrometer.

Thus, according to the present invention, the analysis of the tracer particles or the tracer particle mixture is preferably carried out by optical spectroscopy, IR spectroscopy, plasmonic resonance, microscopy, dosimetry, nuclear magnetic resonance, electron spin resonance, ENDOR, fluorescence spectroscopy, single molecule fluorescence spectroscopy, atomic fluorescence spectroscopy, luminescence spectroscopy, photoluminescence spectroscopy, chromatography, gas chromatography, liquid chromatography and/or high-performance liquid chromatography (HPLC), or by means of a subsequent reaction, which facilitates the detection of the change in the reporting function.

An advantageous practical method is the combination of two molecules or molecular groups, both of which emit fluorescence light at two different wavelengths, for example when excited in the blue or ultraviolet spectral range. One of the two different molecules or molecular groups is stable against the possible environmental conditions in the porous medium, whereas the other one is destroyed or irreversibly changed in its fluorescence properties when certain ambient conditions are reached. If then a tracer particle containing both molecules or molecular groups, after passing through the porous medium and after reaching the conditions required for the change in the detection, it turns out that the fluorescence of the former molecule is unchanged, but the latter not. Thus, it is also possible to exactly determine quantitatively how many percent of all particles have reached the threshold value for the change of the second molecule on the way through the porous medium.

The method according to the present invention is thus used in the characterization of rocks, rock layers and/or porous materials or layers of this porous material, in the geological examination of rocks, rock layers and/or porous materials or layers of this porous material, in the hydrology, aquatic exploration, reservoir exploration, reservoir monitoring, oil detection, fracking, geothermal energy, leak detection, but also in the monitoring of chemical, biological and/or biotechnological reactors, or in medical in vivo procedures.

Technically, for example, the use of particulate moisture sensors should play an important role. Also, the detection of oil in the rock (change of the reporting function by the presence of (traces of) oil) is technically highly relevant. The same applies to the detection of heavy metals. Here, the porous medium might be the soil in the vicinity of a landfill or in the drainage radius of a drinking water storage. A potential application is also to ensure the seal or the leakage location in landfills, hazardous waste landfills and other deposits. If such tracer particles are introduced into the stored product at specific locations, it is possible, for example, to find such particles in the groundwater or in landfill waste water, and the places where the leak occurred can be precisely identified. This also applies to the long-term monitoring of leakage from car washes, radioactive or chemically contaminated pipelines or cisterns. Monitoring can be extremely cost-effective and continuous. The process is suitable for non-destructive intrusion detection of porous media and their property control (to ensure quality and performance in production), exploration of oil, natural gas, natural resources, geothermal, porosity, and low-cost non-destructive exploration of rocks, e.g. in the field of tunneling.

The method according to the present invention is also particularly suitable for use in chemical and biological/ biotechnological reactors as well as water tanks, water storage and water supply systems. In these applications, the interior of the chemical and biological/biotechnological reactors as well as the interior of the water tanks, water reservoirs and water supply systems are to be understood as the "porous medium".

As a specific use, for example, the review of whether a maximum temperature is exceeded in chemical reactors may be mentioned. This is of great interest, for example, in polymerization reactions where thermal decomposition products and carbon are formed when certain temperature values are exceeded, which adversely affects the color of the resulting polymer, and also the electrical insulation properties, for instance. With the method according to the present invention, it can be determined whether and to what extent such temperature excesses took place. Both the temperature values that were exceeded can be determined with the tracer particles with the appropriate threshold in the reporting function, as well as the extent of the overshoot. Specifically, how many percent of the particles, after leaving the reactor, have experienced the excess of their reporting function.

The investigation can also be carried out by spectroscopy of the particles directly in the corresponding reaction product leaving the reactor, or by subsequent extraction of the tracer particles from the reaction product leaving the reactor, e.g. by ultracentrifugation or by extraction of ferromagnetic particles by means of a magnetic field.

In addition, another possibility is that the method according to the present invention is used in medical in vivo methods. The fluid with the tracer particles is injected into a human or animal body in order to carry out diagnostic procedures on the bloodstream, lymphatic system, urinary system, digestive tract, lung and respiratory tract, nose and sinuses, for instance.

The present invention will be further illustrated in the following examples without being limited thereto.

EXAMPLES

Reference Example 1—Dense Silica Nanoparticles (NPs) with Embedded Fluorescent Molecules or Quantum Dots Via a Stöber Synthesis The nanoparticles can be synthesized with a core-shell architecture, encapsulated by a paraffin hull as shown in FIG. 9, part (a). The core is composed of dense silica, in which a fluorescent dye A (fluorescent molecule or quantum dot)—here by way of example, tris(2,2-bipyridyl)dichloro-ruthenium(II) hexahydrate (Ru(bpy)$_3^{2+}$), absorption maximum at 452 nm, emission maximum at 612 nm—is embedded.

The nanoparticle synthesis starts with a modified Stöber synthesis with tetraethyl orthosilicate (TEOS) and (3-aminopropyl)triethoxysilane (ATPES) as the silica precursors, in the presence of Ru(bpy)$_3^{2+}$. Here, a mixture of H$_2$O, ethylenglycol and ammonium hydroxide solution are stirred and heated to 60° C. After reaching 60° C., the fluorescent dye is added gradually together with TEOS at a steady rate over one minute. 30 minutes later, ATPES is added. The synthesis is continued for 4 hours with stirring at 60° C. Now, dense silica nanoparticles with embedded Ru(bpy)$_3$ have formed. The particles are collected by centrifugation at 6000 rpm, washed with water and ethanol, dried under vacuum and weighed. They were then stored in water for 72 hours at temperatures up to 200° C. and a pressure of up to 15 bar in water for stability testing. Since the Ru(bpy)$_3^{2+}$ is the reference function, which has to be stable throughout the experiment, it is important to ensure that the fluorescent dye does not leak out or bleach over time or when exposed to high temperatures.

FIG. 10, part (a) shows the emission spectrum (excitation wavelength 452 nm) of four 0.1 mg ml$^{-1}$ solutions of Ru(bpy)$_3^{2+}$ doped silica nanoparticles after 72 hours in an autoclave at different conditions ranging from room temperature and atmospheric pressure (purple curve) to 100° C. and 1.01 bar (blue curve), 150° C. and 4.76 bar (red curve) and 200° C. and 15.55 bar (black curve). The fluorescence spectroscopy confirms that the emission intensities of all solutions are similar, regardless of the conditions they had been exposed to. This proves that the silica core effectively encapsulates and protects the signaling/reference function within the inspected temperature and pressure range. That is, the fluorescent dye is embedded in the core and does not leak and is protected from degradation under ambient conditions typical to geothermal reservoirs, for instance.

Details on the above reaction conditions are also given in Synthesis Example 1.

Reference Example 2—Dense Silica Nanoparticles (NPs) with Embedded Fluorescent Molecules or Quantum Dots Via Reverse Microemulsion To a mixture of 7.5 ml of cyclohexane, 1.8 ml of n-hexanol, 1.77 ml of Triton X 100, 0.48 ml Ru(bpy)$_3$ in H$_2$O is added by way of example (fluorescent molecule or quantum dot is both possible). With stirring, 0.1 ml of TEOS is added and stirred for 20 minutes. This is followed by adding 0.06 ml of 25% ammonium hydroxide solution. After stirring for 24 hours, silica nanoparticles with embedded Ru(bpy)$_3$ have formed. The solution is made up with 14 ml of acetone and centrifuged at 6000 rpm. This is followed by 3 washes (1× acetone, 2× ethanol), dried under vacuum and weighed.

Reference Example 3—Silica Nanoparticles (NPs) with Embedded Fluorescent Dye Droplets Via a Stöber Synthesis To a mixture of 50 ml of H$_2$O, 50 mg of cetrimonium bromide (CTAB), 0.344 ml of 30% ammonium hydroxide solution, 3 mg rhodamine B are added by way of example and stirred for 10 minutes. Dropwise, a mixture of 0.5 ml APTES, 0.5 ml TEOS and 1.5 ml ethanol are added. After 12 hours, mesoporous silica particles have formed, which can be dried and weighed after centrifugation and washing 3 times with H$_2$O.

Reference Example 4—Paraffin Hull

The dried silica nanoparticles (50 mg) are stored open after addition of a fluorescent dye B (here 17 mg Safranin O) in a glove box under nitrogen atmosphere with exclusion of water for 4 hours to reduce the residual water content in the mixture of nanoparticles and ink. It is followed by addition of 2.5 ml of acetonitrile, the solution is sealed and stirred for 12 hours. The sample is removed from the glove box and 0.375 ml of n-octadecyltrimethoxysilane is added to modify and functionalize the surface of the nanoparticles. After 12 hours, the particles are centrifuged off, washed with hexane and dried under vacuum. Thereafter, they are dispersed in 40 ml of hexane by means of ultrasound and 375 mg of a paraffin are added. The choice of paraffin determines the selected temperature threshold (see list of paraffins). The mixture is sonicated for 20 minutes and stirred for a further 20 minutes. The nanoparticles are collected by centrifugation and dried under vacuum. After drying, the particles are dissolved in water. In order to make the paraffin-coated nanoparticles soluble in water, an anionic surfactant (for example, sodium dodecyl sulfate (SDS)) is added. This deposits on the surface of the paraffin and does not dissolve even by repeated washing with water. The particles are now ready for use.

Reference Example 5—Metal Hull

The silica nanoparticles are functionalized on their surface by means of aminopropyl trimethoxysilane (APTMS) with an amino group. Then, with tetrakis(hydroxymethyl)-phosphonium chloride (THPC) encapsulated gold nanoparticles are added, which bind to the amino groups. These in turn serve as nuclei for electroless deposition of metals on the surface. For example, by adding $Cu^{2+}$ ions from cupric sulfate ($CuSO_4$) and adding formaldehyde under alkaline conditions, a copper hull can be produced, as it is described in H. Wang et al., J. Phys. Chem. B, 2005, 109 (39), 18218-18222.

Reference Example 6—Polymer Pore Blockers

The pores of the mesoporous silica nanoparticle can be closed by various polymers. Thus, by electrostatic coating with multiple layers of a polyelectrolyte pair of sodium polystyrene sulfonates (PSS) and polycation poly (allylamine hydrochloride) (PAH), a layer can be formed which is impermeable at a neutral or basic pH, but which becomes permeable at a pH of 1.5.

Another possibility is coordinated polymerization with, for example, zinc and 1,4-bis(imidazol-1-ylmethyl)benzene (BIX) grown on the nanoparticle surface (BIX-Zn architecture). The coordinated bonds between BIX and Zn can be broken by $H^+$. This layer becomes permeable at low pH values. Similarly, other polymers can also be used which are separated from the particle by predetermined pH thresholds or temperature thresholds.

The above modifications are described for instance in the following articles:

Y. Zhu et al., Angewandte Chemie, 2005, 117 (32), 5213-5217; and L. Xing et al., Adv. Mater., 2012, 24 (48), 6433-6437.

Reference Example 7—Lipid Hull

For example, silica nanoparticles can be coated with a bilayer of zwitterionic dioleoylphosphatidylcholine (DOPC) and negatively charged dioleoylphosphatidylserine (DOPS) (4:1 weight ratio). This layer separates from the particle at the melting point of the lipid layer.

The above modification is described for instance in the following article:

S. Mornet et al., Nano Letters, 2005, 5 (2), 281-285.

Reference Example 8—Grafted Polymer Brush

Various polymer brushes can be grafted onto a silica surface. This can happen, for example, by the functionalization of the end group of a polymer brush with a silane group, which then binds to the surface via hydrolysis and binding to the —OH group of the silica particle. Also, the modification of the silica is conceivable with a self-assembling monolayer having a functional end group. In this case, for example, APTES can serve for an amine end group or 3-(trimethoxysilyl) propyl methacrylate (MPS) can serve for a double bond. The modified end groups can then chemically react with the end group of the functional group of the polymer brushes to bind them to the surface.

Polymer brushes can be expanded and folded by external influences and stimuli. Examples of these are poly(2-(dimethylamino)ethyl methacrylate) (PDMAEMA) brushes, which expand in water and fold at the interface with oil, or poly[(N-isopropylacrylamide)-co-(methacrylic acid)] (P(NIPAm-co-MAA)) brushes which fold at a pH below 5 or at temperatures above 45° C. When grafted onto mesoporous silica nanoparticles, such polymer brushes can prevent the release of fluorescent dyes in the particle by expanding, while allowing the same dye to pass through when folded.

Reference Example 9—Magnetic Fluorescent Nanoparticle Core by Embedding of Iron Oxide Nanoparticle In a reverse-microemulsion reaction, iron (III) oxide powder is dissolved in cyclohexane and Triton X-100, hexanol and water ($H_2O$) are added under stirring. As is common in microemulsion reactions, the formation of the emulsion is followed by addition of the silica precursor tetraethoxy orthosilicate (TEOS) and later aqueous ammonia (28~30 wt.-%) is introduced to initiate the TEOS hydrolysis. After 24 h, additional TEOS and the solution of the fluorescent dye 1-(3-trimethoxysilylpropyl)-N-fluorosceyl thiourea (FITC-APTMS) in ethanol are added. After allowing the reagents enough time to react, the microemulsion system is broken by adding ethanol. Nanoparticles that are composed of a 10 nm magnetic iron oxide core surrounded by fluorescent dye-embedded silica can be collected by centrifugation and washed. The above modification is described for instance in the following article:

C. W. Lu et al., Nano Letters, 2007, 7 (1), 149-154.

Reference Example 10—Attaching Ion Chelating Agents to the Surface of Silica Nanoparticles 5-(tert-butoxy)-5-oxo-4-(4,7,10-tris(2-(tert-butoxy)-2-oxoethyl)-1,4,7,10-tetraazacyclododecan-1-yl)pentanoic acid (DOTAGA(tBu)$_4$), which is a chelating agent for gadolinium, is dissolved in dichloromethane (DCM) with stirring, then N,N-diisopropylethylamine (DIPEA) is added followed by the coupling agents 2-(1H-benzotriazol-1-yl)-1,1,3,3-tetramethyluronium hexafluorophosphate (HBTU) and hydroxybenzotriazole (HOBt) at room temperature. After 15 minutes (3-aminopropyl)triethoxysilane (APTES) is added to be coupled with the DOTAGA(tBu)$_4$ to form DOTAGA(tBu)4-APTES, which is then washed and subsequently isolated by evaporation of the solvent. The t-Bu protection groups are then removed to expose the carboxylic acid groups by concentrated HCl, which is then evaporated at 35° C. in vacuum. The product of DOTAGA-APTES is now ready for use for self-assembly on the surface of silica nanoparticles. The DOGATA-APTES is dissolved in dimethylsulfoxide (DMSO), to which a suspension of nanoparticles is added. In a typical silane chemical reaction, the DOGATA-APTES self assembles on the surface of the silica nanoparticles, which are then collected and washed. The above modification is described for instance in the following articles: A. Mignot et al., Chemistry A European Journal, 2013, 19 (19), 6122-6136 and V. L. Tran et al., Contrast Media & Molecular Imaging, 2018 (2018).

Synthesis Example 1

A mixture of 9.5 ml $H_2O$, 1.45 ml ethylenglycol (Sigma Aldrich, 99.8%), and 0.42 ml 28-30% ammonium hydroxide solution (Merck) are stirred and heated to 60° C. 25 mg of tris(2,2-bipyridyl)dichlororuthenium(II) hexahydrate (Ru $(bpy)_3^{2+}$) is added together with 0.33 ml of tetraethyl orthosilicate (TEOS, Aldrich, 99.0%), which is gradually added dropwise at a steady rate over one minute. 30 minutes later, 60 µl of (3-aminopropyl)triethoxysilane (ATPES, Aldrich, 99%) are added. After 4 hours of continued stirring and heating to 60° C. $Ru(bpy)_3^{2+}$-doped silica nanoparticles (SiNPs) are formed.

The synthesis of the silica shell, which contains the reporting function, proceeds in the same reaction pot by the addition 60 mg of cetrimonium bromide (CTAB, Merck, 97.0%) and 30 minutes later of a mixture of 0.33 ml TEOS and 0.66 ml APTES. After a further 90 minutes, the inner $Ru(bpy)_3^{2+}$-doped SiNPs are coated with an external layer of silica with CTAB micelles entrapped in it. The solution is then collected, centrifuged at 6000 rpm, and undergoes 3 wash-centrifugation cycles with $H_2O$, ethanol and methanol as solvents. The particles are then resuspended in methanol and the CTAB micelles are extracted by refluxing for 16 hours in a mixture of 120 ml methanol (VWR Chemicals, 99.9%), 2.48 ml $H_2O$ and 1.24 ml hydrochloric acid (HCl, Fluka 36.5-38%) under stirring and heating to 70° C. (pH 0.9), to leave pores in the silica shell, which are subsequently loaded with Safranin O, before being encapsulated in a paraffin hull. The particles are then collected by centrifugation at 6000 rpm and washed by methanol and ethanol. The particles are then vacuum dried for at least 3 hours and weighed.

Figure 11:
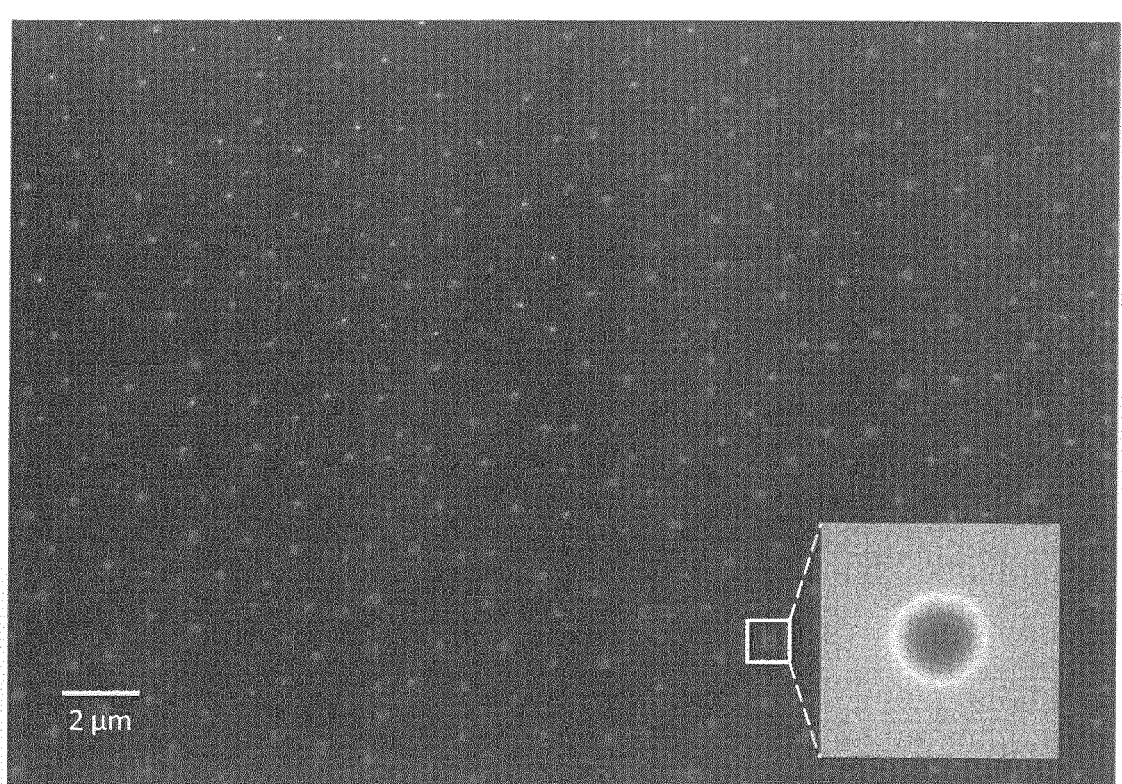
FIG. 11: SEM imaging of the obtained particles of Synthesis Example 1.

SEM imaging of the obtained particles shows that the synthesis yielded round particles with an average diameter value of 188±59 nm as shown in FIG. 11. The $Ru(bpy)_3^{2+}$ emission of the nanoparticles was detected in clean water solutions at standard measurement conditions even at concentrations as low as 1.3 ng ml$^{-1}$ with a signal-to-noise ratio of 5.3.

These NPs are stored in a water free environment (desiccator purged with dry nitrogen or argon or in a glovebox with $H_2O$ levels lower than 50 ppb), where 17 mg Safranin O (Acros Organics, 95%) is added to 50 mg of NPs. After 2 hours, dry acetonitrile is added and the solution is sealed to prevent adsorption of water from the air and is stirred for at least 12 hours. 0.375 ml of n-octadecyltrimethoxysilane (ABCR GmbH, 95%) is added to render the surface of the nanoparticles hydrophobic. The solution is further stirred for at least 12 hours, then the NPs are collected by centrifugation and are washed with acetonitrile (Merck, 99.5%) and hexane (Carl Roth, 99%), following which they are vacuum dried. When the NPs are dry, they are resuspended in 40 ml hexane and 375 mg of paraffin is added to the mixture (all 3 paraffins are manufactured by Aldrich, tetracosane 99%, dotriacontane 97%, tetratetracontane 99%) in accordance with the temperature threshold that is required (see Table 4). The mixture is sonicated for 15 minutes and stirred for 15 minutes, following which the paraffin-coated NPs are collected by centrifugation and dried in vacuum. When the NPs are dry, they are re-suspended in water with sodium dodecyl sulfate (SDS, Sigma-Aldrich 99.0%) and undergo 2-3 centrifugation wash cycles with $H_2O$ until the residual Safranin O is washed away and the supernatant is clear. The particles are then ready for use.

Nanoparticles suspension: The nanoparticles may be difficult to dissolve along the steps of the above described multiple-step synthesis, especially after they were vacuum dried or centrifuged. To re-suspend the particles, the reaction vessels or centrifugation tubes were vortexed and sonicated. When needed, a sonotrode (IUP200St, Hielscher Ultrasonics) was applied as well. This process was regulated by a temperature sensor immersed in the solution to make sure the solution does not exceed the melting point (Mp) of the paraffin during the sonication process. Likewise, longer sonications in sonication baths were performed while maintaining the bath water at room temperature using a circulation thermostat.

Fluorescence spectroscopy: fluorescence spectroscopy was conducted using a Cary Eclipse Fluorescence Spectrophotometer (Agilent Technologies, USA). In-situ heating was conducted by warming the sample holder with a circulation of heating liquid and immersing a temperature probe in the nanoparticle solution.

Evaluation

Figure 12:
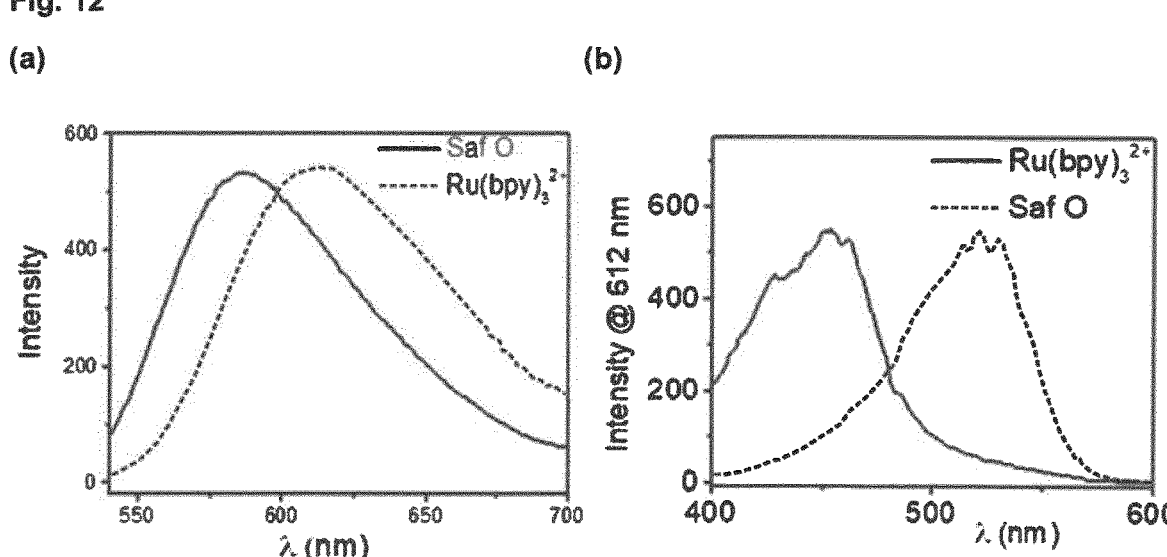
FIG. 12: Part (a) The overlapping fluorescence emissions of Safranin O (upon excitation at a wavelength of 530 nm, black curve) and Ru(bpy)$_3^{2+}$ (upon excitation at a wavelength of 452 nm, red curve), and part (b) fluorescence spectroscopy of Ru(bpy)$_3^{2+}$ (black curve) and Safranin O (red curve) dye solutions, conducted by sweeping the excitation wavelength and measuring the resulting emission at the 612 nm wavelength.

Three different threshold temperatures using different paraffin hulls could be detected: tetracosane ($CH_3$ $(CH_2)_{22}CH_3$, Mp 49-52° C.), dotriacontane ($CH_3$ $(CH_2)_{30}CH_3$, Mp 65-70° C.) and tetratetracontane ($CH_3$ $(CH_2)_{42}CH_3$, Mp 85-87° C.). Monitoring of the dye release process by fluorescence spectroscopy was conducted by sweeping the excitation wavelength and measuring the resulting emission at the 612 nm wavelength. While the emission spectra of $Ru(bpy)_3^{2+}$ and Safranin O largely overlap as shown in FIG. 12, part (a), the excitation wavelengths are distinctly separated. Both $Ru(bpy)_3^{2+}$ and Safranin O show significant emission at 612 nm and it is therefore possible to de-convolute the discrete fluorescence contribution of each dye, based on the fluorescence spectra of each dye separately as shown in FIG. 12, part (b). The ratio of the Safranin O to $Ru(bpy)_3^{2+}$ fluorescence signals (reporting function to reference function, in short: "report/ref") is calculated for each batch of synthesized particles.

Upon heating the nanoparticles to temperatures above the melting point of the paraffin, the Safranin O stored in the mesoporous silica shell is released into the solution. As a result of the Safranin O molecules no longer concentrated in a confined space, photon absorption efficiency increases and fluorescence quenching decreases, thus leading to an increase in emission and subsequently to an increase in the report/ref ratio.

FIG. 10, part (b) shows in-situ fluorescence measurements conducted over 4 hours of heating tetracosane-coated nanoparticles to the tetracosane melting point of 52° C. As Safranin O is released over time, the report/ref ratio increases from an initial ratio of 0.96 to 33.5. In FIG. 10, part (c), the results of a similar experiment with dotriacontane-coated nanoparticles are displayed, with a solution that is heated to 61° C. (i.e. about 4° C. below the melting point) on the left and a solution of similar concentration that is heated to 74° C. (i.e. about 4° C. above the melting point) on the right. Over 4 hours of heating, the report/ref ratio of the 74° C. solution gradually increases from 18.84 to 30.32. In comparison, for the 61° C., the ratio slightly decreases over the first hour, and stabilizes around values of 15.5.

FIG. 10, part (d) shows a comparison of the evolution over time of the report/ref ratio between the 74° C. solution (red curve) and the 61° C. (black curve), normalized to the initial ratio. A summary of the change in the report/ref ratio upon heating to above the melting point of the paraffin hulls for particles with tetracosane, dotriacontane and tetratetracontane hulls is shown in Table 4. The table also includes the corresponding ratios for unheated particles and particles heated to temperatures slightly below the relevant melting point.

TABLE 4

Ratios of the reference to the reporting fluorescence signal of
Ru(bpy)$_3^{2+}$ core - Safranin O shell - paraffin hull nanoparticles
with different paraffin hulls at room temperature, heated slightly
below the Mp of the paraffin hull and slightly above it

| Type of nanoparticle hull [Mp in ° C.] | report/ref ratio at room temperature | report/ref ratio slightly below Mp | report/ref ratio slightly above Mp |
|---|---|---|---|
| Tetracosane (49-52) | 0.95 | 4.15 (at 45° C.) | 33.5 (at 52° C.) |
| Dotriacontane (65-70) | 18.8 | 15.5 (at 61° C.) | 30.3 (at 74° C.) |
| Tetratetracontane (85-87) | 4.04 | 5.31 (at 81° C.) | 43.3 (at 89° C.) |

As a further demonstration of the selective dye release process from the nanoparticle shell upon heating, FIG. 13, part (a) shows two centrifugation tubes containing dotriacontane-coated nanoparticle solutions of identical concentrations (2 mg nanoparticles per ml) after centrifugation. The tube on the left was held at room temperature while the tube on the right was heated to 74° C. As is even evident to the naked eye, fluorescence spectroscopy of the supernatant after centrifugation (excitation wavelength 530 nm) shows that a significantly larger amount of Safranin O was released in the heated solution while only traces were detected in the room temperature solution (FIG. 13, part (b)). No Ru(bpy)$_3^{2+}$ was detected in either of the solutions.

While the results demonstrate that dye release indeed takes place upon heating to temperatures above the melting point of the paraffin hull, it is important to note that detection onsite after reservoir percolation would not be dependent on identification of the dye release itself, but rather on identification of the recovered nanoparticles. In the same experiment shown in FIG. 13, part (a), the nanoparticle pellets were dried and re-suspended to make new solutions of similar concentrations. The room temperature nanoparticles had a pink hue, typical of the Safranin O dye, and displayed a report/ref ratio of 19.01, whereas the heated nanoparticles had an orange tone, typical of the Ru(bpy)$_3^{2+}$ dye, and displayed a report/ref ratio of 0.99 (FIG. 13, parts (c) and (d)).

The invention claimed is:

1. A tracer particle having a core-shell structure and having at least a reference function and a reporting function, wherein the particle comprises a core, a mesoporous shell layer and at least one diffusion resistant threshold-triggered hull encapsulating the core-shell structure, wherein the reference function, which is embedded in the core and/or in the mesoporous shell layer, serves to recognize the particle and as stable signal relative to the variable reporting function, the reference function being a fluorescent or luminescent marker, wherein the mesoporous shell layer includes the reporting function which changes irreversibly, depending on an experienced physical, chemical and/or biochemical parameter, the reporting function being a fluorescent or luminescent marker having a different excitation signal or emission signal than the reference function, wherein the hull encapsulating the core-shell structure is diffusion resistant until a specific threshold in the physical, chemical and/or biochemical parameter has been reached and which is stimuli-responsive triggered by the threshold, upon which the hull dissolves, becomes permeable or temporarily permeable, breaks or separates from the core-shell structure, inducing an irreversible change in the reporting function, and wherein the tracer particle further comprises a charged species, which is attached to the diffusion resistant threshold-triggered hull or which is integrated into the core and/or the mesoporous shell layer.

2. The tracer particle according to claim 1, wherein the mesoporous shell layer is a mesoporous silica layer or a mesoporous polymer layer.

3. The tracer particle according to claim 1, wherein the core is a micro- or nanoparticle comprising at least one selected from the group consisting of a metal, a metal oxide, silica, carbon and polymer.

4. The tracer particle according to claim 1, wherein the diffusion resistant threshold-triggered hull is composed of a fusible material selected from the group consisting of paraffins, lipids, metals, metal alloys, absorbed polymers and grafted polymer brushes, which melts, softens, dissolves or changes structure at a certain temperature range or in a certain temperature range.

5. The tracer particle according to claim 1, wherein the diffusion resistant threshold-triggered hull is composed of a polymeric material selected from the group consisting of absorbed polymers, grafted polymer brushes, coordination polymers and polyelectrolytes, which dissolves or becomes permeable when it exceeds or falls below a certain pH or a certain ion concentration.

6. The tracer particle according to claim 1, wherein the diffusion resistant threshold-triggered hull is composed of an oil-soluble substance which dissolves or swells on contact with oil.

7. The tracer particle according to claim 1, further comprising an additional element showing a time-dependent decay or a time-dependent change of a property.

8. The tracer particle according to claim 1, further comprising an additional magnetic function by comprising magnetic nanoparticles embedded in the core and/or in the mesoporous shell layer.

9. The tracer particle according to claim 1, wherein at least one of fluorescent molecules, and quantum dots are embedded in the core as the reference function.

10. A composition comprising at least one tracer particle or a mixture of at least two different kinds of tracer particles according to claim 1, and a fluid, wherein the fluid is selected from the group consisting of water, aqueous solutions, oil, and oil-water mixture or emulsion, a generated or natural gas stream, a liquid-gas mixture, and vapor.

11. The composition according to claim 10, wherein the mixture of the at least two different kinds of tracer particles comprises tracer particles having different particle sizes.

12. A method of quantifying a porous medium with the composition according to claim 10 for detecting physical, chemical or biochemical parameters of the porous medium, which method comprises the following steps:
introducing the composition into the porous medium; and
permeating or passing the composition through the porous medium, wherein the at least one reporting function of the tracer particles changes depending on an experienced physical, chemical or biochemical parameter when reaching a threshold value of the parameter to be detected, while the reference function of the tracer particles remains unchanged, and
after exiting the porous medium, at least one subsequent analysis of the tracer particles on the physically, chemically or biochemically modified reporting function and the reference function of the tracer particles, wherein the reference function serves ter for recognizing the tracer particles.

13. A method for the characterization of one or more of a rock, a rock layer, a porous material, or a layer of the porous material, the method comprising:

introducing the tracer particle of claim 1 into one or more of the rock, the rock layer, the porous material, or the layer of the porous material permeating or passing the composition through the rock, the rock laver, the porous material, or the layer of the porous material, wherein the at least one reporting function of the tracer particle changes depending on an experienced physical, chemical or biochemical parameter when reaching a threshold value of the parameter to be detected, while the reference function of the tracer particle remains unchanged, and after exiting the rock, the rock layer the porous material, or the layer of the porous material, at least one subsequent analysis of the tracer particle on the physically, chemically or biochemically modified reporting function and the reference function of the tracer particle, wherein the reference function serves for recognizing the tracer particle.

*     *     *     *     *